Figure 1:
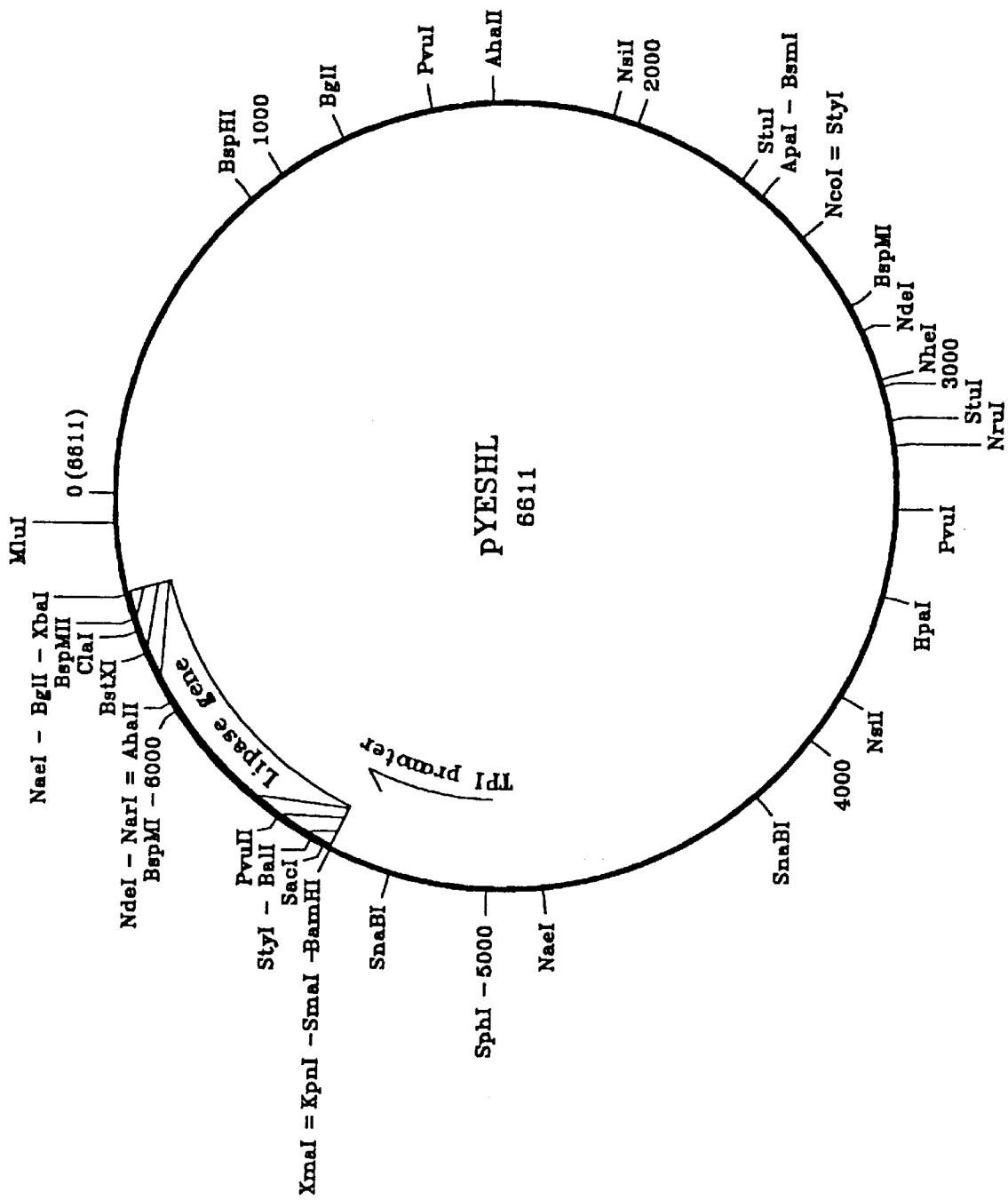

United States Patent [19]

Svendsen et al.

[11] Patent Number: 5,976,855
[45] Date of Patent: *Nov. 2, 1999

[54] METHOD OF PREPARING A VARIANT OF A LIPOLYTIC ENZYME

[75] Inventors: Allan Svendsen, Birkerød; Ib Groth Clausen, Hillerød; Jens Sigurd Okkels; Marianne Thellersen, both of Frederiksberg C, all of Denmark

[73] Assignee: Novo Nordisk A/S, Bagsvært, Denmark

[ * ] Notice: This patent issued on a continued prosecution application filed under 37 CFR 1.53(d), and is subject to the twenty year patent term provisions of 35 U.S.C. 154(a)(2).

[21] Appl. No.: 08/701,339

[22] Filed: Aug. 22, 1996

Related U.S. Application Data

[63] Continuation of application No. PCT/DK95/00079, Feb. 22, 1995.

[30] Foreign Application Priority Data

Feb. 22, 1994 [DK] Denmark ................................. 0217/94

[51] Int. Cl.$^6$ ............................... C12N 9/20; C12N 1/20; C12N 1/00; C07H 21/04
[52] U.S. Cl. ..................... 435/198; 435/69.1; 435/252.3; 435/320.1; 435/471; 435/832; 435/849; 435/874; 435/886; 435/913; 435/911; 536/23.2
[58] Field of Search ..................................... 435/198, 832, 435/849, 874, 886, 913, 471, 69.1, 252.3, 320.1; 536/23.2

[56] References Cited

U.S. PATENT DOCUMENTS 4,600,693  7/1986  Kindle et al. ........................... 435/176

FOREIGN PATENT DOCUMENTS

| 525 610 A2 | 7/1992 | European Pat. Off. |
| WO 92/05249 | 4/1992 | WIPO . |
| WO 94/14964 | 7/1994 | WIPO . |

OTHER PUBLICATIONS

Abstract—Dialog; File 155, Medline, Dialog Accession No. 06804243.

*Primary Examiner*—Robert A. Wax
*Assistant Examiner*—Tekchand Saidha
*Attorney, Agent, or Firm*—Steve T. Zelson, Esq.; Elias J. Lambiris, Esq.

[57] ABSTRACT

The present invention relates to a method of preparing a variant of a parent lipolytic enzyme, comprising (a) subjecting a DNA sequence encoding the parent lipolytic enzyme to random mutagenesis, (b) expressing the mutated DNA sequence obtained in step (a) in a host cell, and (c) screening for host cells expressing a mutated lipolytic enzyme which has a decreased dependance to calcium and/or an improved tolerance towards a detergent or a detergent component as compared to the parent lipolytic enzyme.

21 Claims, 5 Drawing Sheets

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
       (A) LENGTH: 918 base pairs
       (B) TYPE: nucleic acid
       (C) STRANDEDNESS: single
       (D) TOPOLOGY: linear (ii) MOLECULE TYPE: cDNA (vi) ORIGINAL SOURCE:
       (A) ORGANISM: Humicola lanuginosa (ix) FEATURE:
       (A) NAME/KEY: CDS
       (B) LOCATION: 1..873
       (C) NAME/KEY: mat_peptide
       (D) LOCATION: 67..873

(xi) SEQUENCE DESCRIPTION: SEQ ID NO:1:

```
ATG AGG AGC TCC CTT GTG CTG TTC TTT GTC TCT GCG TGG ACG GCC TTG         48
Met Arg Ser Ser Leu Val Leu Phe Phe Val Ser Ala Trp Thr Ala Leu
        -20                 -15                 -10

GCC AGT CCT ATT CGT CGA GAG GTC TCG CAG GAT CTG TTT AAC CAG TTC         96
Ala Ser Pro Ile Arg Arg Glu Val Ser Gln Asp Leu Phe Asn Gln Phe
     -5                   1                   5

AAT CTC TTT GCA CAG TAT TCT GCA GCC GCA TAC TGC GGA AAA AAC AAT        144
Asn Leu Phe Ala Gln Tyr Ser Ala Ala Ala Tyr Cys Gly Lys Asn Asn
        10                  15                  20

GAT GCC CCA GCT GGT ACA AAC ATT ACG TGC ACG GGA AAT GCC TGC CCC        192
Asp Ala Pro Ala Gly Thr Asn Ile Thr Cys Thr Gly Asn Ala Cys Pro
 25                  30                  35                  40

GAG GTA GAG AAG GCG GAT GCA ACG TTT CTC TAC TCG TTT GAA GAC TCT        240
Glu Val Glu Lys Ala Asp Ala Thr Phe Leu Tyr Ser Phe Glu Asp Ser
                45                  50                  55

GGA GTG GGC GAT GTC ACC GGC TTC CTT GCT CTC GAC AAC ACG AAC AAA        288
Gly Val Gly Asp Val Thr Gly Phe Leu Ala Leu Asp Asn Thr Asn Lys
                60                  65                  70

TTG ATC GTC CTC TCT TTC CGT GGC TCT CGT TCC ATA GAG AAC TGG ATC        336
Leu Ile Val Leu Ser Phe Arg Gly Ser Arg Ser Ile Glu Asn Trp Ile
        75                  80                  85

GGG AAT CTT AAC TTC GAC TTG AAA GAA ATA AAT GAC ATT TGC TCC GGC        384
Gly Asn Leu Asn Phe Asp Leu Lys Glu Ile Asn Asp Ile Cys Ser Gly
 90                  95                 100

TGC AGG GGA CAT GAC GGC TTC ACT TCG TCC TGG AGG TCT GTA GCC GAT        432
Cys Arg Gly His Asp Gly Phe Thr Ser Ser Trp Arg Ser Val Ala Asp
105                 110                 115                 120

ACG TTA AGG CAG AAG GTG GAG GAT GCT GTG AGG GAG CAT CCC GAC TAT        480
Thr Leu Arg Gln Lys Val Glu Asp Ala Val Arg Glu His Pro Asp Tyr
                125                 130                 135

CGC GTG GTG TTT ACC GGA CAT AGC TTG GGT GGT GCA TTG GCA ACT GTT        528
Arg Val Val Phe Thr Gly His Ser Leu Gly Gly Ala Leu Ala Thr Val
                140                 145                 150

GCC GGA GCA GAC CTG CGT GGA AAT GGG TAT GAT ATC GAC GTG TTT TCA        576
Ala Gly Ala Asp Leu Arg Gly Asn Gly Tyr Asp Ile Asp Val Phe Ser
        155                 160                 165

TAT GGC GCC CCC CGA GTC GGA AAC AGG GCT TTT GCA GAA TTC CTG ACC        624
Tyr Gly Ala Pro Arg Val Gly Asn Arg Ala Phe Ala Glu Phe Leu Thr
        175                 180                 185
```

```
GTA CAG ACC GGC GGA ACA CTC TAC CGC ATT ACC CAC ACC AAT GAT ATT        672
Val Gln Thr Gly Gly Thr Leu Tyr Arg Ile Thr His Thr Asn Asp Ile
190                 195                 200                 205

GTC CCT AGA CTC CCG CCG CGC GAA TTC GGT TAC AGC CAT TCT AGC CCA        720
Val Pro Arg Leu Pro Pro Arg Glu Phe Gly Tyr Ser His Ser Ser Pro
                210                 215                 220

GAG TAC TGG ATC AAA TCT GGA ACC CTT GTC CCC GTC ACC CGA AAC GAT        768
Glu Tyr Trp Ile Lys Ser Gly Thr Leu Val Pro Val Thr Arg Asn Asp
            225                 230                 235

ATC GTG AAG ATA GAA GGC ATC GAT GCC ACC GGC GGC AAT AAC CAG CCT        816
Ile Val Lys Ile Glu Gly Ile Asp Ala Thr Gly Gly Asn Asn Gln Pro
        240                 245                 250

AAC ATT CCG GAT ATC CCT GCG CAC CTA TGG TAC TTC GGG TTA ATT GGG        864
Asn Ile Pro Asp Ile Pro Ala His Leu Trp Tyr Phe Gly Leu Ile Gly
    255                 260                 265

ACA TGT CTT TAGTGGCCGG CGCGGCTGGG TCCGACTCTA GCGAGCTCGA GATCT          918
Thr Cys Leu
270
```

(2) INFORMATION FOR SEQ ID NO:2:

(i) SEQUENCE CHARACTERISTICS:
        (A) LENGTH: 291 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Ser Ser Leu Val Leu Phe Phe Val Ser Ala Trp Thr Ala Leu
        -20                 -15                 -10

Ala Ser Pro Ile Arg Arg Glu Val Ser Gln Asp Leu Phe Asn Gln Phe
    -5                   1               5                   10

Asn Leu Phe Ala Gln Tyr Ser Ala Ala Ala Tyr Cys Gly Lys Asn Asn
                15                  20                  25

Asp Ala Pro Ala Gly Thr Asn Ile Thr Cys Thr Gly Asn Ala Cys Pro
                30                  35                  40

Glu Val Glu Lys Ala Asp Ala Thr Phe Leu Tyr Ser Phe Glu Asp Ser
                45                  50                  55

Gly Val Gly Asp Val Thr Gly Phe Leu Ala Leu Asp Asn Thr Asn Lys
        60                  65                  70

Leu Ile Val Leu Ser Phe Arg Gly Ser Arg Ser Ile Glu Asn Trp Ile
75                  80                  85                  90

Gly Asn Leu Asn Phe Asp Leu Lys Glu Ile Asn Asp Ile Cys Ser Gly
                95                  100                 105

Cys Arg Gly His Asp Gly Phe Thr Ser Ser Trp Arg Ser Val Ala Asp
            110                 115                 120

Thr Leu Arg Gln Lys Val Glu Asp Ala Val Arg Glu His Pro Asp Tyr
        125                 130                 135

Arg Val Val Phe Thr Gly His Ser Leu Gly Gly Ala Leu Ala Thr Val
    140                 145                 150

Ala Gly Ala Asp Leu Arg Gly Asn Gly Tyr Asp Ile Asp Val Phe Ser
155                 160                 165                 170

Tyr Gly Ala Pro Arg Val Gly Asn Arg Ala Phe Ala Glu Phe Leu Thr
                175                 180                 185

Val Gln Thr Gly Gly Thr Leu Tyr Arg Ile Thr His Thr Asn Asp Ile
                190                 195                 200

Val Pro Arg Leu Pro Pro Arg Glu Phe Gly Tyr Ser His Ser Ser Pro
            205                 210                 215
```

```
Glu Tyr Trp Ile Lys Ser Gly Thr Leu Val Pro Val Thr Arg Asn Asp
220                 225                 230

Ile Val Lys Ile Glu Gly Ile Asp Ala Thr Gly Gly Asn Asn Gln Pro
235                 240                 245                 250

Asn Ile Pro Asp Ile Pro Ala His Leu Trp Tyr Phe Gly Leu Ile Gly
                255                 260                 265

Thr Cys Leu
```

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TATTTCTTTC AAAGCGAACT TAAGATTCCC GAT                                  33

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GGTCATCCAG TCACTGAGAC CCTCTACCTA TTAAATCGGC                      40

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CCATGGCTTT CACGGTGTCT                                                  20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GGTCATCCAG TCACTGAGAC                                                  20

(2) INFORMATION FOR SEQ ID NO:7:

(i) SEQUENCE CHARACTERISTICS:
        (A) LENGTH: 65 base pairs
        (B) TYPE: nucleic acid
        (C) STRANDEDNESS: single
        (D) TOPOLOGY: linear

37

(ii) MOLECULE TYPE: cDNA (xi) SEQUENCE DESCRIPTION: SEQ ID NO:7:

ATTTCTTTCA AAGCGAACTT AAGATTCCCG ATCCAGTTCT CTATGGAACG AGTGCCACGG　　　60

AAAGA　　　65

(2) INFORMATION FOR SEQ ID NO:8:

(i) SEQUENCE CHARACTERISTICS:
　　　　　(A) LENGTH: 54 base pairs
　　　　　(B) TYPE: nucleic acid
　　　　　(C) STRANDEDNESS: single
　　　　　(D) TOPOLOGY: linear (ii) MOLECULE TYPE: cDNA (xi) SEQUENCE DESCRIPTION: SEQ ID NO:8:

TATTTCTTTC AAAACGAAGT TAAGATTCCC GATCCAGTTC TTTATGGAAC GAGA　　　54

(2) INFORMATION FOR SEQ ID NO:9:

(i) SEQUENCE CHARACTERISTICS:
　　　　　(A) LENGTH: 54 base pairs
　　　　　(B) TYPE: nucleic acid
　　　　　(C) STRANDEDNESS: single
　　　　　(D) TOPOLOGY: linear (ii) MOLECULE TYPE: cDNA (xi) SEQUENCE DESCRIPTION: SEQ ID NO:9:

TATTTCTTTC AAAGCGAAGT TAAGATTAGC GATCCAGTTC TTTATGGAAC GAGA　　　54

(2) INFORMATION FOR SEQ ID NO:10:

(i) SEQUENCE CHARACTERISTICS:
　　　　　(A) LENGTH: 33 base pairs
　　　　　(B) TYPE: nucleic acid
　　　　　(C) STRANDEDNESS: single
　　　　　(D) TOPOLOGY: linear (ii) MOLECULE TYPE: cDNA (xi) SEQUENCE DESCRIPTION: SEQ ID NO:10:

TATTTCTTTC AAGTGCAACT TAAGATTCCC GAT　　　33

(2) INFORMATION FOR SEQ ID NO:11:

(i) SEQUENCE CHARACTERISTICS:
　　　　　(A) LENGTH: 30 base pairs
　　　　　(B) TYPE: nucleic acid
　　　　　(C) STRANDEDNESS: single
　　　　　(D) TOPOLOGY: linear (ii) MOLECULE TYPE: cDNA (xi) SEQUENCE DESCRIPTION: SEQ ID NO:11:

TATTTCTTTC AAGTTACAGT TAAGATTCCC　　　30

(2) INFORMATION FOR SEQ ID NO:12:

(i) SEQUENCE CHARACTERISTICS:
　　　　　(A) LENGTH: 42 base pairs
　　　　　(B) TYPE: nucleic acid
　　　　　(C) STRANDEDNESS: single
　　　　　(D) TOPOLOGY: linear (ii) MOLECULE TYPE: cDNA (xi) SEQUENCE DESCRIPTION: SEQ ID NO:12:

TATTTCTTTC AAGTCACAGT TAACATTAGA GATCCAGTTC TC                42

(2) INFORMATION FOR SEQ ID NO:13:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

TATTTCTTTC AAAGCGAACT TAATATTAGC GATCCAGTTC TTTATGGAAC GAGA    54

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

ATATGAAAAC ACACCGATAT CATACCC                                 27

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CCTTAACGTA TCAACTACAG ACCTCCA                                 27

(2) INFORMATION FOR SEQ ID NO:16:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GCTGTAACCG AATTGGCGCG GCGGGAGCTT AGGGACAATA TC                42

(2) INFORMATION FOR SEQ ID NO:17:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TATTTCTTTC AAAGCGAACT TAAGATTAGC GATCCAGTTC TTTATAGTAC GAGAGCCACG    60

GAAAGAGAGG ACGATCAATT TGTCCGTGTT GTCGAG                              96

(2) INFORMATION FOR SEQ ID NO:18:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
TATTTCTTTC AAAACGAACT TAAGATTAGC GATACCGTTC TTTATGGAAC GAGTGCCACG    60

GAAAGA                                                              66
```

(2) INFORMATION FOR SEQ ID NO:19:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
GCAAATGTCA TTAACTTCTT TCAATCTGAA GTTAAGATTA GCGATCCAGT TCTTTATGGA    60

ACGAGA                                                              66
```

(2) INFORMATION FOR SEQ ID NO:20:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

```
CCCGATCCAG TTCTTTATGG AACGAGTGCC ACGGAAAGA                           39
```

(2) INFORMATION FOR SEQ ID NO:21:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
GAAGTTAAGA TTAGCGATCC AGTTCTTTAT GGAACGAGA                           39
```

(2) INFORMATION FOR SEQ ID NO:22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

```
CCCGATCCAG TTCTTTATGG AACGAGTGCC ACGGAAAGA                           39
```

(2) INFORMATION FOR SEQ ID NO:23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

```
CGGAATGTTA GGTCTGTTAT TGCCGCC                                        27
```

METHOD OF PREPARING A VARIANT OF A LIPOLYTIC ENZYME

CROSS-REFERENCE TO RELATED APPLICATIONS

This application is a continuation of PCT/DK95/00079 filed Feb. 22, 1995, which is incorporated herein by reference.

FIELD OF THE INVENTION

The present invention relates to a method of preparing a variant of a parent lipolytic enzyme and to variants prepared by the method. Furthermore, the invention relates to a DNA construct encoding a variant of the invention, an expression vector and host cell comprising the DNA construct and a detergent additive or a detergent composition comprising a variant.

BACKGROUND OF THE INVENTION

For a number of years lipolytic enzymes have been used as detergent enzymes, i.e., to remove lipid or fatty stains from clothes and other textiles.

For instance, various microbial lipases have been suggested as detergent enzymes. Examples of such lipases include a *Humicola lanuginosa* lipase, e.g., described in EP 258 068 and EP 305 216, a *Rhizomucor miehei* lipase, e.g., as described in EP 238 023, a Candida lipase, such as a *C. antarctica* lipase, e.g., the *C. antarctica* lipase A or B described in EP 214 761, a Pseudomonas lipase such as a *P. alcaligenes* and *P. pseudoalcaligenes* lipase, e.g., as described in EP 218 272, a *P. cepacia* lipase, e.g., as described in EP 331 376, a Bacillus lipase, e.g., a *B. subtilis* lipase (Dartois et al., 1993), a *B. stearothermophilus* lipase (JP 64/744992) and a *B. pumilus* lipase (EP 91 00664).

Furthermore, a number of cloned lipases have been described, including the *Penicillium camembertii* lipase described by Yamaguchi, S. et al., 1991, the *Geotricum candidum* lipase (Schimada, Y. et al., 1989), and various Rhizopus lipases such as a *R. delemar* lipase (Hass, M. J et al., 1991), a *R. niveus* lipase (Kugimiya, W. 1992), and a *R. oryzae* lipase.

Other types of lipolytic enzymes having been suggested as detergent enzymes include cutinases, e.g., derived from *Pseudomonas mendocina* as described in WO 88/09367, or a cutinase derived from *Fusarium solani pisi* (e.g., described in WO 90/09446).

In recent years attempts have been made to prepare lipase variants having improved properties for detergent purposes. For instance, WO 92/05249 discloses lipase variants with improved properties, in which certain characteristics of wild-type lipase enzymes have been changed by specific, i.e., site-directed modifications of their amino acid sequences. More specifically, lipase variants are described, in which one or more amino acid residues of the so-called lipid contact zone of the parent lipase has been modified.

PCT/DK93/00225 describes lipase variants with improved properties, in which an amino acid residue occupying a critical position of the lipase has been modified.

EP 407 225 discloses lipase variants with improved resistance towards proteolytic enzymes, which have been prepared by specifically defined amino acid modifications.

EP 260 105 describe hydrolases in which an amino acid residue within 15 Å from the active site has been substituted.

All of the above mentioned lipase variants have been constructed by use of site-directed mutagenesis resulting in a modification of specific amino acid residues which have been chosen either on the basis of their type or on the basis of their location in the secondary or tertiary structure of the parent lipase.

An alternative approach for constructing mutants or variants of a given protein has been based on random mutagenesis. For instance, U.S. Pat. No. 4,898,331 and WO 93/01285 disclose such techniques.

A need exists for novel lipolytic enzymes having improved washing and/or dishwashing properties, and the object of the present invention is to prepare such enzymes.

BRIEF DISCLOSURE OF THE INVENTION

The present inventors have now developed a novel method of preparing variants of lipolytic enzymes having improved washing and/or dishwashing performance as compared to their parent enzymes. The method is based on random or localized random mutagenesis of DNA sequences encoding a lipolytic enzyme.

More specifically, in a first aspect the invention relates to a method of preparing a variant of a parent lipolytic enzyme, which method comprises (a) subjecting a DNA sequence encoding the parent lipolytic enzyme to random mutagenesis, (b) expressing the mutated DNA sequence obtained in step (a) in a host cell, and (c) screening for host cells expressing a mutated lipolytic enzyme which has a decreased dependence to calcium and/or an improved tolerance towards a detergent or one or more detergent components as compared to the parent lipolytic enzyme.

In the present context, the term "lipolytic enzyme" is intended to indicate an enzyme exhibiting a lipid degrading capability, such as a capability of degrading a triglycerid or a phospholipid. The lipolytic enzyme may, e.g., be a lipase, a phospholipase, an esterase or a cutinase.

The term "random mutagenesis" is intended to be understood in a conventional manner, i.e., to indicate an introduction of one or more mutations at random positions of the parent enzyme (i.e., as opposed to site-specific mutagenesis). The random mutations are typically introduced by exposing a large number of copies of the DNA sequence to be modified to a mutagen and then screening for the presence of variants. Suitable techniques for introducing random mutations are discussed in detail below.

The screening criteria of step c) are considered to be of particular use in identifying variants of parent lipolytic enzymes having improved washing and/or dishwashing performance as compared to their parent enzymes.

In the present context, the term "decreased dependence to calcium" is intended to mean that the mutated lipolytic enzyme requires lower amounts of calcium for exhibiting the same degree of activity as the parent enzyme when tested under similar conditions. Preferably, the mutated lipolytic enzyme of the invention is substantially independant of the presence of calcium for exhibiting enzymatic activity.

The term "improved tolerance towards a detergent or detergent component" is intended to mean that the mutated lipolytic enzyme is active at higher concentrations of the detergent or detergent component than the parent lipolytic enzyme.

In the present context the term "detergent" is intended to indicate a mixture of detergent ingredients normally used for washing or dishwashing. Analogously, a "detergent component" is intended to indicate a component or ingredient normally found in detergent or dishwashing compositions, examples of which are given in the following description.

It will be understood that the variant prepared by the method of the invention in addition to the decreased dependency to calcium and/or improved tolerance towards a detergent or one or more detergent components exhibits lipolytic activity preferably of a magnitude comparable to or exceeding that of the parent lipolytic enzyme, when tested under washing and/or dishwashing conditions.

The screening criteria defined in step c) of the method of the invention may be determined by any suitable methods known in the art. A particular suitable assay developed for the present purpose is described in the Materials and Methods section below.

In a further aspect the invention relates to a DNA construct comprising a mutated DNA sequence encoding a variant of a lipolytic enzyme which has a decreased dependance to calcium and/or an improved tolerance towards a detergent or a detergent component as compared to the parent lipolytic enzyme, which DNA sequence is isolated from the host cell selected in step (c) of the method of the invention.

In a still further aspect the invention relates to a recombinant expression vector carrying the DNA construct, a cell which is transformed with the DNA construct or the vector as well as a method of producing the variant of the parent lipolytic enzyme by culturing said cell under conditions conducive to the production of the variant, after which the variant is recovered from the culture.

In final aspects the invention relates to a variant of a lipolytic enzyme and the use of said variant as a detergent enzyme, in particular for washing or dishwashing, and to a detergent additive and a detergent composition comprising the variant.

DETAILED DISCLOSURE OF THE INVENTION

Cloning a DNA Sequence Encoding a Parent Lipolytic Enzyme

The DNA sequence encoding a parent lipolytic enzyme to be subjected to random mutagenesis in accordance with the present invention may be isolated from any cell or microorganism producing the parent enzyme in question by use of methods known in the art.

For instance, the DNA sequence may be isolated by establishing a cDNA or genomic library from an organism expected to harbour the sequence, and screening for positive clones by conventional procedures. Examples of such procedures are hybridization to oligonucleotide probes prepared on the basis of the amino acid or DNA sequence of the parent enzyme (if sequence information is available) or of a related lipolytic enzyme (if sequence information as to the parent enzyme is not available) in accordance with standard techniques (cf. Sambrook et al., 1989), and/or selection for clones expressing lipolytic, such as lipase activity, and/or selection for clones producing a protein which is reactive with an antibody raised against a parent lipolytic enzyme.

A preferred method of isolating a DNA sequence encoding a parent lipolytic enzyme to be modified in accordance with the invention from a cDNA or genomic library is by use of polymerase chain reaction (PCR) using degenerate oligonucleotide probes prepared on the basis of DNA or amino acid sequence of the parent enzyme. For instance, the PCR may be carried out using the techniques described in U.S. Pat. No. 4,683,202 or by R. K. Saiki et al. (1988).

Alternatively, the DNA sequence encoding the parent enzyme may be prepared synthetically by established standard methods, e.g., the phosphoamidite method described by Beaucage and Caruthers (1981), or the method described by Matthes et al. (1984). According to the phosphoamidite method, oligonucleotides are synthesized, e.g., in an automatic DNA synthesizer, purified, annealed, ligated and cloned in appropriate vectors.

Finally, the DNA sequence encoding the parent enzyme may be prepared from DNA of mixed genomic and synthetic, mixed synthetic and cDNA or mixed genomic and cDNA origin prepared by ligating fragments of synthetic, genomic or cDNA origin (as appropriate), the fragments corresponding to various parts of the entire DNA sequence encoding the parent enzyme, in accordance with standard techniques.

Random Mutagenesis

The random mutagenesis of the DNA sequence encoding the parent lipolytic enzyme to be performed in accordance with step a) of the method of the invention may conveniently be performed by use of any method known in the art.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents.

The mutagenizing agent may, e.g., be one which induces transitions, transversions, inversions, scrambling, deletions, and/or insertions.

Examples of a physical or chemical mutagenizing agent suitable for the present purpose includes ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions wanted to be changed. The doping or spiking may be done so that codons for unwanted amino acids are avoided. The doped or spiked oligonucleotide can be incorporated into the DNA encoding the lipolytic enzyme by any published technique using e.g., PCR, LCR or any DNA polymerase and ligase.

When PCR generated mutagenesis is used either a chemically treated or non-treated gene encoding a parent lipolytic enzyme is subjected to PCR under conditions that increases the misincorporation of nucleotides (Deshler 1992, Leung et al. 1989).

A mutator strain of E. coli (Fowler et al. 1974), S. cereviciae or any other microbial organism may be used for the random mutagenesis of the DNA encoding the lipolytic enzyme by e.g., transforming a plasmid containing the parent enzyme into the mutator strain, growing the mutator strain with the plasmid and isolating the mutated plasmid from the mutator strain. The mutated plasmid may subsequently be transformed into the expression organism.

The DNA sequence to be mutagenized may conveniently be present in a genomic or cDNA library prepared from an organism expressing the parent lipolytic enzyme. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to the expression step (b) or the screening step (c) being performed. Such amplification may be performed in accordance with methods known in the art, the presently preferred method being PCR generated amplification using oligonucleotide primers prepared on the basis of the DNA or amino acid sequence of the parent enzyme.

Subsequent to the incubation with or exposure to the mutagenizing agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are given below. The mutated DNA sequence may further comprise a DNA sequence encoding functions permitting expression of the mutated DNA sequence.

It will be understood that the screening criteria mentioned in step (c) above have been carefully selected. Thus, without being limited to any theory the screening for a decreased dependency to calcium is believed to result in variants having an over-all improved performance in that the requirement for calcium may be considered a limiting factor for optimal activity, in particular under conditions where only low amounts of free calcium ions are present. In connection with detergent lipases the free calcium ions required are normally provided from the washing water and thus, the lipolytic activity is dependent on the calcium content of the water.

The detergent or detergent component towards which the variant has improved tolerance may be of any type, e.g., as further described below. Preferably, the detergent component is a non-ionic, anionic, kationic, zwitterionic or amphoteric surfactant. Examples of non-ionic surfactants include an alcohol ethoxylate, examples of anionic surfactants include LAS, alkyl sulphate, alcohol ethoxy sulphate and the like.

In particular, it is contemplated that an improved tolerance towards a non-ionic surfactant alcohol ethoxylate, a commercially available example of which is Dobanol®, may be indicative of improved wash performance.

The screening of step (c) is conveniently performed by use of a filter assay based on the following principle:

A microorganism capable of expressing the mutated lipolytic enzyme of interest is incubated on a suitable medium and under suitable conditions for the enzyme to be secreted, the medium being provided with a double filter comprising a first protein-binding filter and on top of that a second filter exhibiting a low protein binding capability. The microorganism is located on the second filter. Subsequent to the incubation, the first filter comprising enzymes secreted from the microorganisms is separated from the second filter comprising the microorganisms. The first filter is subjected to screening for the desired enzymatic activity and the corresponding microbial colonies present on the second filter are identified.

The filter used for binding the enzymatic activity may be any protein binding filter e.g., nylon or nitrocellulose. The topfilter carrying the colonies of the expression organism may be any filter that has no or low affinity for binding proteins e.g., cellulose acetate or Durapore™. The filter may be pretreated with any of the conditions to be used for screening or may be treated during the detection of enzymatic activity.

The enzymatic activity may be detected by a dye, flourescence, precipitation, pH indicator, IR-absorbance or any other known technique for detection of enzymatic activity.

The detecting compound may be immobilized by any immobilizing agent e.g., agarose, agar, gelatine, polyacrylamide, starch, filter paper, cloth; or any combination of immobilizing agents.

Lipase activity may be detected by Brilliant green, Rhodamine B or Sudan Black in combination with a lipid e.g., olive oil or lard. The screening criteria for identifying variants of parent lipolytic enzymes having improved washing performance may be e.g., EGTA, EDTA, non-ionic or anionic tensides, alkaline pH, or any detergent composition in combination with one of the above detectors of enzymatic activity.

It will be understood that the screening criteria used in the filter assay of the invention may be chosen so as to comply with the desired properties or uses of the enzymes to be screened. For instance, in a screening for lipases of particular use in the paper and pulp industry, it may be relevant to screen for an acid lipase having an increased temperature stability. This may be performed by using a buffer with acidic pH (e.g., pH 4) and/or incubate under higher temperature before or under the assay.

The host cells produced in step (c) may be subjected to further rounds of mutagenesis as defined in steps (a)–(c) above, conveniently by using more stringent selection criteria than employed in a previous mutagenesis treatment.

The host cells selected for in step (c) may be used directly for the production of the variant of the lipolytic enzyme. Alternatively, DNA encoding the variant may be isolated from the host cell and inserted into another suitable host cell, conveniently by use of the procedure described below in the section entitled "Expression of a variant of the invention", in which suitable host cells are also listed.

Localized Random Mutagenesis

In accordance with the invention the random mutagenesis may advantageously be located to a part of the parent lipolytic enzyme in question. This may, e.g., be advantageous when a certain region of the enzyme has been identified to be of particular importance for a given property of the enzyme, and which, when modified, is expected to result in a variant having improved properties. Such region may normally be identified when the tertiary structure of the parent enzyme has been elucidated and related to the function of the enzyme.

The localized random mutagenesis is conveniently performed by use of PCR generated mutagenesis techniques as described above or any other suitable technique known in the art.

Alternatively, the DNA sequence encoding the part of the DNA sequence to be modified may be isolated, e.g., by being inserted into a suitable vector, and said part may subsequently be subjected to mutagenesis by use of any of the mutagenesis methods discussed above.

The Parent Lipolytic Enzyme

The parent lipolytic enzyme to be modified in accordance with the invention may be any enzyme which has lipolytic activity as defined above. Examples of lipolytic enzymes includes a lipase, an esterase, a cutinase and a phospholipase.

Preferably, the parent lipolytic enzyme is modified by localized random mutagenesis performed on a part of the DNA sequence encoding a lipid contact zone or a part of said zone.

All lipases crystalized until now have been found to comprise at least one surface loop structure (also termed a lid or a flap) which covers the active site when the lipase is in inactive form (an example of such a lipase is described by Brady et al., 1990). When the lipase is activated, the loop structure is shifted to expose the active site residues, and a hydrophobic surface is created surrounding the active site Ser, which has an increased surface hydrophobicity and which interacts with the lipid substrate at or during hydrolysis. This activation is termed interfacial activation and is further discussed by Tilbeurgh et al. (1993).

For the present purpose, the surface created upon activation is termed the "lipid contact zone", intended to include amino acid residues located within or forming part of this surface, optionally in the form of loop structures. These residues may participate in lipase interaction with the substrate at or during hydrolysis where the lipase hydrolyses triglycerides from the lipid phase when activated by contact with the lipid surface.

Figure 2:
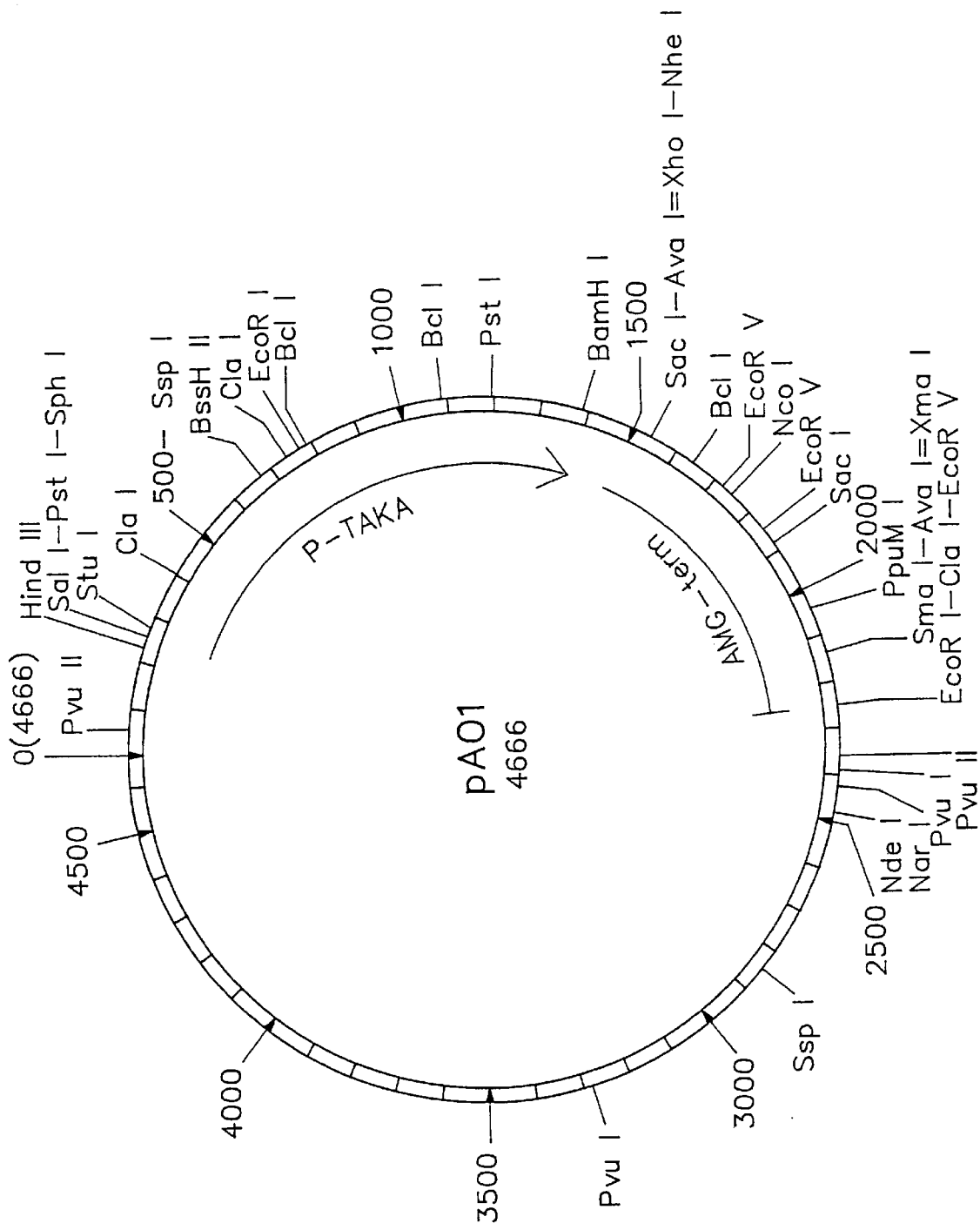

The lipid contact zone contains a binding area for the lipid substrate which is the part of the lipid contact zone to which the single lipid substrate molecule binds before hydrolysis. This binding area again contains an acyl-binding hydrophobic cleft and a so-called hydrolysis pocket, which is situated around the active site Ser, and in which the hydrolysis of the lipid substrate is believed to take place. In all lipases known today the lipid contact zone is easily recognized, e.g., from a three-dimensional structure of the lipase created by suitable computer programs. The conformation of an inactive and activated lipase, respectively, is shown in FIGS. 1 and 2 of WO 92/05249.

The lipid contact zone of the *Humicola lanuginosa* lipase discussed in detail in the present application is defined by amino acid residues 21–25, 36–38, 56–62, 81–98, 110–116, 144–147, 172–174, 199–213 and 248–269. These residues have been identified on the basis of computer model simulations of the interaction between the lipase and a lipid substrate.

The lipid contact zone of other lipolytic enzymes is defined by a) calculating the hydrophobic vector of the 3-D molecular structure, b) making a cut perpendicular to the vector through the Cα-atom of the second amino acid residue after the active site serine in the linear sequence, and c) including all residues with at least one atom on that side of the cut to which the vector points, and d) selecting from those residues, those which have at least one atom within 5 Ångström of the surface of the protein (in case of a lipase in either its open or closed form).

The hydrophobic vector is calculated from the protein structure, in case of a lipase either the open or closed form, by summing up all residue vectors for residues having a surface accessibility (Lee et al., Mol. Biol. 55, pp. 379–400 (1971)) of at least 10%. The starting point of the residue vector is defined as the Cα-atom of the residue and its direction is through the mass center of the sidechain. The magnitude of each residue vector is defined as the residues relative transfer free energy.

The surface accessibility of each residue is calculated using the Connolly program.

Preferably, the localized random mutagenesis is performed on a part of the DNA sequence encoding a lid region and/or a hydrophobic cleft of the parent lipase, or a part of said lid region and/or hydrophobic cleft.

The parent lipolytic enzyme to be modified in accordance with the invention may be of any origin. Thus, the enzyme may be of mammalian, plant, vertebrate or any other region. However, it is presently preferred that the enzyme is of microbial origin in that a number of microbial strains have been found to produce enzymes of particular use for detergent purposes.

More specifically, the DNA sequence parent lipolytic enzyme may be derived from a fungus, i.e., a yeast or a filamentous fungus. For instance, the DNA sequence may be one which is derivable form a strain of a Humicola sp., e.g., *H. lanuginosa*, a strain of a Rhizomucor sp., e.g., *Rh. miehei*, a strain of a Rhizopus sp., a strain of a Candida sp., a strain of a Fusarium sp., e.g., *F. solani pisi*, a strain of a Venturia spp., e.g., *V. inaequalis*, a strain of a Colletotrichum spp., e.g., *C. gloeosporioides*, or *C. lagenarium*, or a strain of a Penicillium spp., e.g., *P. spinulosum* or *P. camembertii*.

In the present context, "derivable from" is intended not only to indicate an enzyme produced by a strain of the organism in question, but also an enzyme encoded by a DNA sequence isolated from such strain and produced in a host organism transformed with said DNA sequence. Furthermore, the term is intended to indicate an enzyme which is encoded by a DNA sequence of synthetic and/or cDNA origin and which has the identifying characteristics of the enzyme in question.

Of particular interest as a parent lipolytic enzyme is a lipase derivable from a strain of *H. lanuginosa*, e.g., the *H. lanuginosa* strain DSM 4109, or an analogue of said lipase, a strain of *Rh. mucor*, or a strain of *C. antarctica*.

In the present context the term "analogue" is intended to include a polypeptide which comprises an amino acid sequence differing from that of the *H. lanuginosa* lipase by one or more amino acid residues, and which is at least 70% homologous with the amino acid sequence of said lipase, (determined as the degree of identity between the two sequences), such as at least 75%, 80%, 90% or 95% homologous, is immunologically cross reactive with said lipase, and/or which is encoded by a DNA sequence hybridizing with an oligo nucleotide probe prepared on the basis of the amino acid sequence of said lipase or of a DNA sequence encoding said lipase.

The analogue may be a derivative of the *H. lanuginosa* lipase, e.g., prepared by modifying a DNA sequence encoding the lipase resulting in the addition of one or more amino acid residues to either or both the N- and C-terminal end of the lipase, substitution of one or more amino acid residues at one or more different sites in the amino acid sequence, deletion of one or more amino acid residues at either or both ends of the lipase or at one or more sites in the amino acid sequence, or insertion of one or more amino acid residues at one or more sites in the amino acid sequence. The modification of the DNA sequence may be performed by site-directed or by random mutagenesis or a combination of these techniques in accordance with well-known procedures.

Furthermore, the analogue may be a polypeptide derived from another organism such as one of those mentioned in the section "Background of the invention" above.

The hybridization of a DNA sequence encoding an analogue of the parent *H. lanuginosa* lipase with the relevant oligonucleotide probe(s) may be carried out under any suitable conditions allowing the DNA sequences to hybridize. For instance, such conditions are hybridization under specified conditions, e.g., involving presoaking in 5×SSC and prehybridizing for 1 h at ~40° C. in a solution of 20% formamide, 5×Denhardt's solution, 50 mM sodium phosphate, pH 6.8, and 50 μg of denatured sonicated calf thymus DNA, followed by hybridization in the same solution supplemented with 100 μM ATP for 18 h at ~40° C., or other methods described by e.g., Sambrook et al., 1989.

The immunological cross-reactivity of an analogue of the *H. lanuginosa* lipase may be assayed using an antibody raised against or reactive with at least one epitope of the purified lipase. The antibody, which may either be monoclonal or polyclonal, may be produced by methods known in the art, e.g., as described by Hudson et al., 1989. The immunological cross-reactivity may be determined using assays known in the art, examples of which are Western Blotting or radial immunodiffusion assay, e.g., as described by Hudson et al., 1989.

When the parent lipolytic enzyme is the *H. lanuginosa* lipase obtainable from strain DSM 4109 or an analogue thereof, it is preferred that the DNA sequence subjected to random mutagenesis comprises a part of or constitutes a part of a DNA sequence encoding at least one of the regions defined by the amino acid residues 21–27, 56–64, 81–99, 83–100, 108–116, 145–147, 174, 202–213, such as 205–211, 226–227, 246–259 or 263–269 of said lipase. The DNA and amino acid sequence of said lipase is apparent from SEQ ID Nos. 1 and 2, respectively.

The localized random mutagenesis may be performed in one or more of these regions, and is preferably performed in at least two of the regions.

The parent lipolytic enzyme to be modified in accordance with the present invention may be derivable from a bacterium. For instance, the DNA sequence encoding the parent lipolytic enzyme may be derivable from a strain of Pseudomonas spp., such as *P. cepacia, P. alcaligenes, P. pseudoalcaligens, P. mendocina* (also termed *P. putida*), *P. syringae, P. aeroginosa* or *P. fragi*, a strain of Bacillus spp., e.g., *B. subtilis* or *B. pumilus* or a strain of Streptomyces sp., e.g., *S. scabies*.

The parent bacterial lipolytic enzyme may be a lipase derived from any of the above-mentioned species, e.g., a Pseudomonas lipase as described in EP 218 272, EP 331 376 and EP 407 225, or a cutinase, e.g., as described in WO 88/09367.

Variants of the Invention

For ease of reference specific variants of the invention are described by use of the following nomenclature:
Original amino acid(s):position(s):substituted amino acid(s)

According to this nomenclature, for instance the substitution of aspartic acid for valine in position 96 is shown as:
Asp 96 Val or D96V
a deletion of aspartic acid in the same position is shown as:
Asp 96 * or D96*
and insertion of an additional amino acid residue such as lysine is shown as:
Asp 96 ValLys or D96VK Multiple mutations are separated by pluses, i.e.:
Asp 96 Val+Glu 87 Lys or D96V+E87K
representing mutations in positions 96 and 87 substituting aspartic acid and glutamic acid for valine and lysine, respectively.

When one or more alternative amino acid residues may be inserted in a given position it is indicated as D96V,N or D96V or D96N.

Furthermore, when a position suitable for modification is identified herein without any specific modification being suggested, it is to be understood that any amino acid residue may be substituted for the amino acid residue present in the position. Thus, for instance, when a modification of an aspartic acid in position 96 is mentioned, but not specified, it is to be understood that the aspartic acid may be deleted or substituted for any other amino acid, i.e., any one of R,N,A,C,Q,E,G,H,I,L,K,M,F,P,S,T,W,Y,V, or a further amino acid residue inserted at that position.

Finally, when a mutation of the parent *H. lanuginosa* lipase is identified herein, it is intended to be understood as including a similar mutation of an analogue of said lipase (as defined above).

In a further aspect the invention relates to a variant constructed by the above described method of the invention.

When the parent lipolytic enzyme is the *H. lanuginosa* lipase obtainable from strain DSM 4109 or an analogue thereof as defined above, it is preferred that the variant comprises a mutation in at least one of the following positions: S58, T64, S83, N94, K98, I100, A121, E129, D167, R205, K237, I252, P256 or G263.

It will be understood that in case of replacement any amino acid residue other than the wildtype amino acid residue may be inserted, such as an amino acid residue selected from R, N, A, C, Q, E, G, H, I, L, K, M, F, P, S, T, W, Y, V, D.

As far as the present inventors are aware no prior disclosure of specific mutations within these positions exists.

In addition the invention relates to a variant of the *H. lanuginosa* lipase obtainable from DSM 4109 or an analogue of said lipase, wherein the amino acid residue L264 has been replaced by an amino acid different from Leucine, i.e., any one of R, N, A, C, Q, E, G, H, I, K, M, F, P, S, T, W, Y, V, D.

Preferably, the variant according to the invention comprises at least one of the following mutations K46R, E57G, G61S, S83T, S58F, D62C, T64R, I90F, G91A, N92H, N94I, N94K, L97M, K98I, I100V, D102K, A121V, E129K, D167G, R205K, E210W, K237M, N259W, I252L, D254W, P256T, G263A, L264Q or T267W.

These positions have been found or is contemplated to be important for enzymatic activity and/or detergent tolerance. The numbering of the amino acid residues refers to the amino acid sequence of the mature lipase.

Preferably, the variant according to this aspect of the invention comprises at least one of the following mutations S83T, N94K, A121V, D167G, R205K.

It will be understood that the present invention encompasses variants of the parent *H. lanuginosa* lipase comprising a combination of two or more of the mutations defined herein, or a combination of one or more of the mutations defined herein with any of the mutations disclosed in WO 92/05249, WO 94/25577 and WO 94/01541.

In a further aspect the present invention relates to a variant of the *H. lanuginosa* lipase obtainable from DSM 4109 or an analogue thereof comprising at least one of the following mutations:
N94K+D96A
S83T+N94K+D96N
E87K+D96V
E87K+G91A+D96A
N94K+F95L+D96H
A121V+R205K+E210Q
F95C+D96N
G91S+L93V+F95C
E87K+G91A+D96R+I100V
E87K+G91A
S83T+E87K+Q249R
S83T+E87K+W89G+G91A+N94K+D96V
N73D+S85T+E87K+G91A+N94K+D94A
E87K+G91A+L93I+N94K+D96A
D167G+E210V
N73D+E87K+G91A+N94I+D96G
S83T+E87K+G91A+N92H+N94K+D96M
E210W
E56T+D57L+I90F+D96L+E99K E56R+D57L+V60M+D62N+S83T+D96P+D102E
D57G+N94K+K96L+L97M
E87K+G91A+D96R+I100V+E129K+K237M+I252L+
    P256T+G263A+L264Q
E56R+D57G+S58F+D62C+T64R+E87G+G91A+F95L+
    D96P+K98I+K237M
K46R+E56R+G61S
D102K
D167G
N73D+E87K+G91A+N94I+D96G
E210V
E210W
N251W+D254W+T267W
S83T+E87K+G91A+N92H+N94K+D96M
E56R+I90F+D96L+E99K
D57G+N94K+D96L+L97M These variants have been found to exhibit a decreased resistance to calcium and/or an improved tolerance towards detergent components, such as the non-ionic surfactant alcohol ethoxylate and are, accordingly, considered of particular use for detergent or dishwashing purposes. The variants have been constructed by the method of the invention and subsequently characterized with respect to the mutations having been introduced and are further described in the Examples hereinafter. It will be apparent that an alternative method of constructing these variants would be based on site-directed mutagenesis using suitable oligonucleotide probes. This method is exemplified in Examples 3–6.

Expression of a Variant of the Invention

According to the invention, a mutated DNA sequence encoding a variant lipolytic enzyme prepared by methods described above, or any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding a variant of the invention may be any vector which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding a variant of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), e.g., as described in WO 93/10249 the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding a variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g., a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. The parent lipolytic enzyme may in itself comprise a pre-region permitting secretion of the expressed enzyme into the culture medium. If desirable, this preregion may be replaced by a different preregion or signal sequence, convenient accomplished by substitution of the DNA sequences encoding the respective preregions.

The procedures used to ligate the DNA construct of the invention encoding a variant of a parent lipolytic enzyme, the promoter, terminator and other elements, respectively, and to insert them into suitable vectors containing the information necessary for replication, are well known to persons skilled in the art (cf., for instance, Sambrook et al. (1989)).

The cell of the invention either comprising a DNA construct or an expression vector of the invention as defined above is advantageously used as a host cell in the recombinant production of a variant of a parent lipolytic enzyme of the invention. The cell may be transformed with the DNA construct of the invention encoding the variant, conveniently by integrating the DNA construct in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described below in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus*

*coagulans, Bacillus circulars, Bacillus lautus, Bacillus megaterium, Bacillus thuringiensis,* or *Streptomyces lividans* or *Streptomyces murinus*, or gram-negative bacteria such as *E. coli*. The transformation of the bacteria may for instance be effected by protoplast transformation or by using competent cells in a manner known per se.

The yeast organism may favourably be selected from a species of Saccharomyces or Schizosaccharomyces, e.g., *Saccharomyces cerevisiae*. The filamentous fungus may advantageously belong to a species of Aspergillus, e.g., *Aspergillus oryzae, Aspergillus niger* or *Aspergillus nidulans*. Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method of producing a variant of a parent lipolytic enzyme of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the variant of a parent lipolytic enzyme of the invention. Suitable media are available from commercial suppliers or may be prepared according to published recipes (e.g., in catalogues of the American Type Culture Collection).

The variant of the invention secreted from the host cells may conveniently be recovered from the culture medium by well-known procedures including separating the cells from the medium by centrifugation or filtration, and precipitating proteinaceous components of the medium by means of a salt such as ammonium sulphate, followed by chromatographic procedures such as ion exchange chromatography, affinity chromatography, or the like.

Detergent Additive and Composition for Dishwashing and Washing

Due to the decreased dependance to calcium and/or improved tolerance towards detergents or detergent components of the variant of the invention, the variant is particularly well suited for implementation into detergent compositions, e.g., detergent compositions intended for performance in the range of pH 7–13, particularly the range of pH 8–11.

Detergent Compositions

According to the invention, a lipase variant of the invention may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g., as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g., as described in WO 92/06154).

The detergent composition may additionally comprise one or more other enzymes, such as an amylase, a pullulanase, a cutinase, a protease, a cellulase, a peroxidase, an oxidase, (e.g., laccase) and/or another lipase.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e., essentially free of detergent builder.

The detergent may comprise one or more polymers. Examples are carboxymethylcellulose (CMC), poly (vinylpyrrolidone) (PVP), polyethyleneglycol (PEG), poly (vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of, e.g., the amide, imide, or sulfone type.

The enzymes of the detergent composition of the invention may be stabilized using conventional stabilizing agents, e.g., a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil-redeposition agents, dyes, bactericides, optical brighteners, or perfume.

The pH (measured in aqueous solution at use concentration) will usually be neutral or alkaline, e.g., in the range of 7–11.

Particular forms of detergent compositions within the scope of the invention include:

1) A detergent composition formulated as a granulate having a bulk density of at least 600 g/l comprising

| | |
|---|---|
| Linear alkylbenzenesulfonate (calculated as acid) | 7–12% |
| Alcohol ethoxysulfate (e.g., $C_{12-18}$ alcohol, 1–2 EO) or alkyl sulfate (e.g., $C_{16-18}$) | 1–40% |
| Alcohol ethoxylate (e.g., $C_{14-15}$ alcohol, 7 EO) | 5–9% |
| Sodium carbonate (as $Na_2CO_3$) | 14–20% |
| Soluble silicate (as $Na_2O, 2SiO_2$) | 2–6% |
| Zeolite (as $NaAlSiO_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBO_3 \cdot H_2O$) | 11–18% |
| TAED | 2–6% |
| Carboxymethylcellulose | 0–2% |
| Polymers (e.g., maleic/acrylic acid copolymer, PVP, PEG) | 0–3% |
| Enzymes (calculated as pure enzyme protein) | 0.0001–0.1% |
| Minor ingredients (e.g., suds suppressors, perfume, optical, brightener, photobleach) | 0–5% |

2) A detergent composition formulated as a granulate having a bulk density of at least 600 g/l comprising

| | |
|---|---|
| Linear alkylbenzenesulfonate (calculated as acid) | 6–11% |
| Alcohol ethoxysulfate (e.g., $C_{12-18}$ alcohol, 1–2 EO) or alkyl sulfate (e.g., $C_{16-18}$) | 1–3% |
| Alcohol ethoxylate (e.g., $C_{14-15}$ alcohol, 7 EO) | 5–9% |
| Sodium carbonate (as $Na_2CO_3$) | 15–21% |
| Soluble silicate (as $Na_2O,2SiO_2$) | 1–4% |
| Zeolite (as $NaAlSiO_4$) | 24–34% |
| Sodium sulfate (as $Na_2SO_4$) | 4–10% |
| Sodium citrate/citric acid (as $C_6H_5Na_3O_7/C_6H_8O_7$) | 0–15% |
| Carboxymethylcellulose | 0–2% |
| Polymers (e.g., maleic/acrylic acid copolymer, PVP, PEG) | 1–6% |
| Enzymes (calculated as pure enzyme protein) | 0.0001–0.1% |
| Minor ingredients (e.g., suds suppressors, perfume) | 0–5% |

3) A detergent composition formulated as a granulate having a bulk density of at least 600 g/l comprising

| | |
|---|---|
| Linear alkylbenzenesulfonate (calculated as acid) | 5–9% |
| Alcohol ethoxylate (e.g., $C_{12-15}$ alcohol, 7 EO) | 7–14% |
| Soap as fatty acid (e.g., $C_{16-22}$ fatty acid) | 1–3% |
| Sodium carbonate (as $Na_2CO_3$) | 10–17% |
| Soluble silicate (as $Na_2O, 2SiO_2$) | 3–9% |
| Zeolite (as $NaAlSiO_4$) | 23–33% |
| Sodium sulfate (as $Na_2SO4$) | 0–4% |
| Sodium perborate (as $NaBO_3 \cdot H_2O$) | 8–16% |
| TAED | 2–8% |
| Phosphonate (e.g., EDTMPA) | 0–1% |
| Carboxymethylcellulose | 0–2% |
| Polymers (e.g., maleic/acrylic acid copolymer, PVP, PEG) | 0–3% |
| Enzymes (calculated as pure enzyme protein) | 0.0001–0.1% |
| Minor ingredients (e.g., suds suppressors, perfume, optical brightener) | 0–5% |

4) A detergent composition formulated as a granulate having a bulk density of at least 600 g/l comprising

| | |
|---|---|
| Linear alkylbenzenesulfonate (calculated as acid) | 8–12% |
| Alcohol ethoxylate (e.g., $C_{12-15}$ alcohol, 7 EO) | 10–25% |
| Sodium carbonate (as $Na_2CO_3$) | 14–22% |
| Soluble silicate (as $Na_2O, 2SiO_2$) | 1–5% |
| Zeolite (as $NaAlSiO_4$) | 25–35% |
| Sodium sulfate (as $Na_2SO_4$) | 0–10% |
| Carboxymethylcellulose | 0–2% |
| Polymers (e.g., maleic/acrylic acid copolymer, PVP, PEG) | 1–3% |
| Enzymes (calculated as pure enzyme protein) | 0.0001–0.1% |
| Minor ingredients (e.g., suds suppressors, perfume) | 0–5% |

5) An aqueous liquid detergent composition comprising

| | |
|---|---|
| Linear alkylbenzenesulfonate (calculated as acid) | 15–21% |
| Alcohol ethoxylate (e.g., $C_{12-15}$ alcohol, 7 EO or $C_{12-15}$ alcohol, 5 EO) | 12–18% |
| Soap as fatty acid (e.g., oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g., PVP, PEG) | 0–3% |
| Borate (as $B_4O_7$) | 0–2% |
| Ethanol | 0–3% |
| Propylene glycol | 8–14% |
| Enzymes (calculated as pure enzyme protein) | 0.0001–0.1% |
| Minor ingredients (e.g., dispersants, suds suppressors, perfume, optical brightener) | 0–5% |

6) An aqueous structured liquid detergent composition comprising

| | |
|---|---|
| Linear alkylbenzenesulfonate (calculated as acid) | 15–21% |
| Alcohol ethoxylate (e.g., $C_{12-15}$ alcohol, 7 EO,3–9% or $C_{12-15}$alcohol, 5 EO) | |
| Soap as fatty acid (e.g., oleic acid) | 3–10% |
| Zeolite (as $NaAlSiO_4$) | 14–22% |
| Potassium citrate | 9–18% |
| Borate (as $B_4O_7$) | 0–2% |
| Carboxymethylcellulose | 0–2% |
| Polymers (e.g., PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes (calculated as pure enzyme protein) | 0.0001–0.1% |
| Minor ingredients (e.g., dispersants, suds suppressors, perfume, optical brighteners) | 0–5% |

7) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O, 2SiO_2$) | 1–4% |
| Zeolite (as $NaAlSiO_4$) | 20–40% |
| Sodium sulfate (as $Na_2SO_4$) | 2–8% |
| Sodium perborate (as $NaBO_3 \cdot H_2O$) | 12–18% |
| TAED | 2–7% |
| Polymers (e.g., maleic/acrylic acid copolymer, PEG) | 1–5% |
| Enzymes (calculated as pure enzyme protein) | 0.0001–0.1% |
| Minor ingredients (e.g., optical brightener, suds suppressors, perfume) | 0–5% |

8) A detergent composition formulated as a granulate comprising

| | |
|---|---|
| Linear alkylbenzenesulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O, 2SiO_2$) | 1–4% |
| Zeolite (as $NaAlSiO_4$) | 30–50% |
| Sodium sulfate (as $Na_2SO_4$) | 3–11% |
| Sodium citrate (as $C_6H_5Na_3O_7$) | 5–12% |

| | |
|---|---|
| Polymers (e.g., PVP, maleic/acrylic acid copolymer, PEG) | 1–5% |
| Enzymes (calculated as pure enzyme protein) | 0.0001–0.1% |
| Minor ingredients (e.g., suds suppressors, perfume) | 0–5% |

9) A detergent composition formulated as a granulate comprising

| | |
|---|---|
| Linear alkylbenzenesulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaAlSiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaBO_3 \cdot H_2O$) | 4–9% |
| Bleach activator (e.g., NOBS or TAED) | 1–5% |
| Carboxymethylcellulose | 0–2% |
| Polymers (e.g., polycarboxylate or PEG) | 1–5% |
| Enzymes (calculated as pure enzyme protein) | 0.0001–0.1% |
| Minor ingredients (e.g., optical brightener, perfume) | 0–5% |

10) An aqueous liquid detergent composition comprising

| | |
|---|---|
| Linear alkylbenzenesulfonate (calculated as acid) | 15–23% |
| Alcohol ethoxysulfate (e.g., $C_{12-15}$ alcohol, 2–3 EO) | 8–15% |
| Alcohol ethoxylate (e.g., $C_{12-15}$ alcohol, 7 EO, or $C_{12-15}$ alcohol, 5 EO) | 3–9% |
| Soap as fatty acid (e.g., lauric acid) | 0–3% |
| Aminoethanol | 1–5% |
| Sodium citrate | 5–10% |
| Hydrotrope (e.g., sodium toluensulfonate) | 2–6% |
| Borate (as $B_4O_7$) | 0–2% |
| Carboxymethylcellulose | 0–1% |
| Ethanol | 1–3% |
| Propylene glycol | 2–5% |
| Enzymes (calculated as pure enzyme protein) | 0.0001–0.1% |
| Minor ingredients (e.g., polymers, dispersants, perfume, optical brighteners) | 0–5% |

11) An aqueous liquid detergent composition comprising

| | |
|---|---|
| Linear alkylbenzenesulfonate (calculated as acid) | 20–32% |
| Alcohol ethoxylate (e.g., $C_{12-15}$ alcohol, 7 EO, or $C_{12-15}$ alcohol, 5 EO) | 6–12% |
| Aminoethanol | 2–6% |
| Citric acid | 8–14% |
| Borate (as $B_4O_7$) | 1–3% |
| Polymer (e.g., maleic/acrylic acid copolymer, anchoring polymer such as, e.g., lauryl methacrylate/acrylic acid copolymer) | 0–3% |
| Glycerol | 3–8% |
| Enzymes (calculated as pure enzyme protein) | 0.0001–0.1% |
| Minor ingredients (e.g., hydrotropes, dispersants, perfume, optical brighteners) | 0–5% |

12) A detergent composition formulated as a granulate having a bulk density of at least 600 g/l comprising

| | |
|---|---|
| Anionic surfactant (linear alkylbenzenesulfonate, alkyl sulfate, alpha-olefinsulfonate, alpha-sulfo fatty acid methyl esters, alkanesulfonates, soap) | 25–40% |
| Nonionic surfactant (e.g., alcohol ethoxylate) | 1–10% |
| Sodium carbonate (as $Na_2CO_3$) | 8–25% |
| Soluble silicates (as $Na_2O, 2SiO_2$) | 5–15% |
| Sodium sulfate (as $Na_2SO_4$) | 0–5% |
| Xeolite (as $NaAlSiO_4$) | 15–28% |
| Sodium perborate (as $NaBO_3 \cdot 4H_2O$) | 0–20% |
| Bleach activator (TAED or NOBS) | 0–5% |
| Enzymes (calculated as pure enzyme protein) | 0.0001–0.1% |
| Minor ingredients (e.g., perfume, optical brighteners) | 0–3% |

13) Detergent compositions as described in compositions 1–12 wherein all or part of the linear alkylbenzenesulfonate is replaced by ($C_{12}$–$C_{18}$) alkyl sulfate.

14) A detergent composition formulated as a granulate having a bulk density of at least 600 g/l comprising

| | |
|---|---|
| ($C_{12}$–$C_{18}$) alkyl sulfate | 9–15% |
| Alcohol ethoxylate | 3–6% |
| Polyhydroxy alkyl fatty acid amide | 1–5% |
| Zeolite (as $NaAlSiO_4$) | 10–20% |
| Layered disilicate (e.g., SK56 from Hoechst) | 10–20% |
| Sodium carbonate (as $Na_2CO_3$) | 3–12% |
| Soluble silicate (as $Na_2O, 2SiO_2$) | 0–6% |
| Sodium citrate | 4–8% |
| Sodium percarbonate | 13–22% |
| TAED | 3–8% |
| Polymers (e.g., polycarboxylates and PVP) | 0–5% |
| Enzymes (calculated as pure enzyme protein) | 0.0001–0.1% |
| Minor ingredients (e.g., optical brightener, photo bleach, perfume, suds suppressors) | 0–5%% |

15) A detergent composition formulated as a granulate having a bulk density of at least 600 g/l comprising

| | |
|---|---|
| ($C_{12}$–$C_{18}$) alkyl sulfate | 4–8% |
| Alcohol ethoxylate | 11–15% |
| Soap | 1–4% |
| Zeolite MAP or zeolite A | 35–45% |
| Sodium carbonate (as $Na_2CO_3$) | 2–8% |
| Soluble silicate (as $Na_2O, 2SiO_2$) | 0–4% |
| Sodium percarbonate | 13–22% |
| TAED | 1–8% |
| Carboxymethyl cellulose | 0–3% |
| Polymers (e.g., polycarboxylates and PVP) | 0–3% |
| Enzymes (calculated as pure enzyme protein) | 0.0001–0.1% |
| Minor ingredients (e.g., optical brightener, phosphonate, perfume) | 0–3% |

16) Detergent compositions as described in compositions 1–15 which contain a stabilized or encapsulated peracid, either as an additional component or as a substitute for already specified bleach systems.

17) Detergent compositions as described in compositions 1, 3, 7, 9 and 12 wherein perborate is replaced by percarbonate.

18) Detergent compositions as described in compositions 1, 3, 7, 9, 12, 14 and 15 which additionally contain a manganese catalyst. The manganese catalyst may, e.g., be one of the compounds described in "Efficient manganese catalysts for low-temperature bleaching", 1994, *Nature* 369:637–639.

19) Detergent composition formulated as a nonaqueous detergent liquid comprising a liquid nonionic surfactant such as, e.g., linear alkoxylated primary alcohol, a builder system (e.g., phosphate), enzyme and alkali. The detergent may also comprise anionic surfactant and/or a bleach system.

A lipase variant of the invention may be incorporated in concentrations conventionally employed in detergents. It is at present contemplated that, in a detergent composition of the invention, a lipase variant of the invention may be added in an amount corresponding to 0.00001–1 mg (calculated as pure enzyme protein) of the lipase variant per liter of wash liquor.

Dishwashing Composition

The dishwashing detergent composition comprises a surfactant which may be anionic, non-ionic, cationic, amphoteric or a mixture of these types. The detergent will contain 0–90% of non-ionic surfactant such as low- to non-foaming ethoxylated propoxylated straight-chain alcohols.

The detergent composition may contain detergent builder salts of inorganic and/or organic types. The detergent builders may be subdivided into phosphorus-containing and non-phosphorus-containing types. The detergent composition usually contains 1–90% of detergent builders.

Examples of phosphorus-containing inorganic alkaline detergent builders, when present, include the water-soluble salts especially alkali metal pyrophosphates, orthophosphates, polyphosphates, and phosphonates. Examples of non-phosphorus-containing inorganic builders, when present, include water-soluble alkali metal carbonates, borates and silicates as well as the various types of water-insoluble crystalline or amorphous alumino silicates of which zeolites are the best-known representatives.

Examples of suitable organic builders include the alkali metal, ammonium and substituted ammonium, citrates, succinates, malonates, fatty acid sulphonates, carboxymetoxy succinates, ammonium polyacetates, carboxylates, polycarboxylates, aminopolycarboxylates, polyacetyl carboxylates and polyhydroxsulphonates.

Other suitable organic builders include the higher molecular weight polymers and co-polymers known to have builder properties, for example appropriate polyacrylic acid, polymaleic and polyacrylic/polymaleic acid copolymers and their salts.

The dishwashing detergent composition may contain bleaching agents of the chlorine/bromine-type or the oxygen-type. Examples of inorganic chlorine/bromine-type bleaches are lithium, sodium or calcium hypochlorite and hypobromite as well as chlorinated trisodium phosphate. Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water-solubilizing cations such as potassium and sodium. Hydantoin compounds are also suitable.

The oxygen bleaches are preferred, for example in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are TAED and glycerol triacetate.

The dishwashing detergent composition of the invention may be stabilized using conventional stabilizing agents for the enzyme(s), e.g., a polyol such as e.g.propylene glycol, a sugar or a sugar alcohol, lactic acid, boric acid, or a boric acid derivative, e.g., an aromatic borate ester.

The dishwashing detergent composition may also comprise other enzymes, in particular an amylase, a protease and/or a cellulase.

The dishwashing detergent composition of the invention may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescers, thickeners and perfumes.

Finally, the variant of the invention may be used in conventional dishwashing detergents, e.g., any of the detergents described in any of the following patent publications: EP 551670, EP 533239, WO 9303129, EP 507404, U.S. Pat. No. 5,141,664, GB 2247025, EP 414285, GB 2234980, EP 408278, GB 2228945, GB 2228944, EP 387063, EP 385521, EP 373851, EP 364260, EP 349314, EP 331370, EP 318279, EP 318204, GB 2204319, EP 266904, U.S. Pat. No. 5,213, 706, EP 530870, CA 2006687, EP 481547, EP 337760, WO 93/14183, U.S. Pat. No. 5,223,179, WO 93/06202, WO 93/05132, WO 92/19707, WO 92/09680, WO 92/08777, WO 92/06161, WO 92/06157, WO 92/06156, WO 91/13959, EP 399752, U.S. Pat. No. 4,941,988, U.S. Pat. No. 4,908,148.

Furthermore, the lipase variants of the invention may be used in softening compositions.

The lipase variant may be used in fabric softeners, e.g., as described in Surfactant and Consumer Products, Ed. by J. Falbe, 1987, pp 295–296; Tenside Surfactants Detergents, 30 (1993), 6, pp 394–399; JAOCS, Vol. 61 (1984), 2, pp 367–376; EP 517 762; EP 123 400; WO 92/19714; WO 93/19147; U.S. Pat. No. 5,082,578; EP 494 769; EP 544 493; EP 543 562; U.S. Pat. No. 5,235,082; EP 568 297; EP 570 237.

The invention is further described in the accompanying drawings in which

Figure 3:
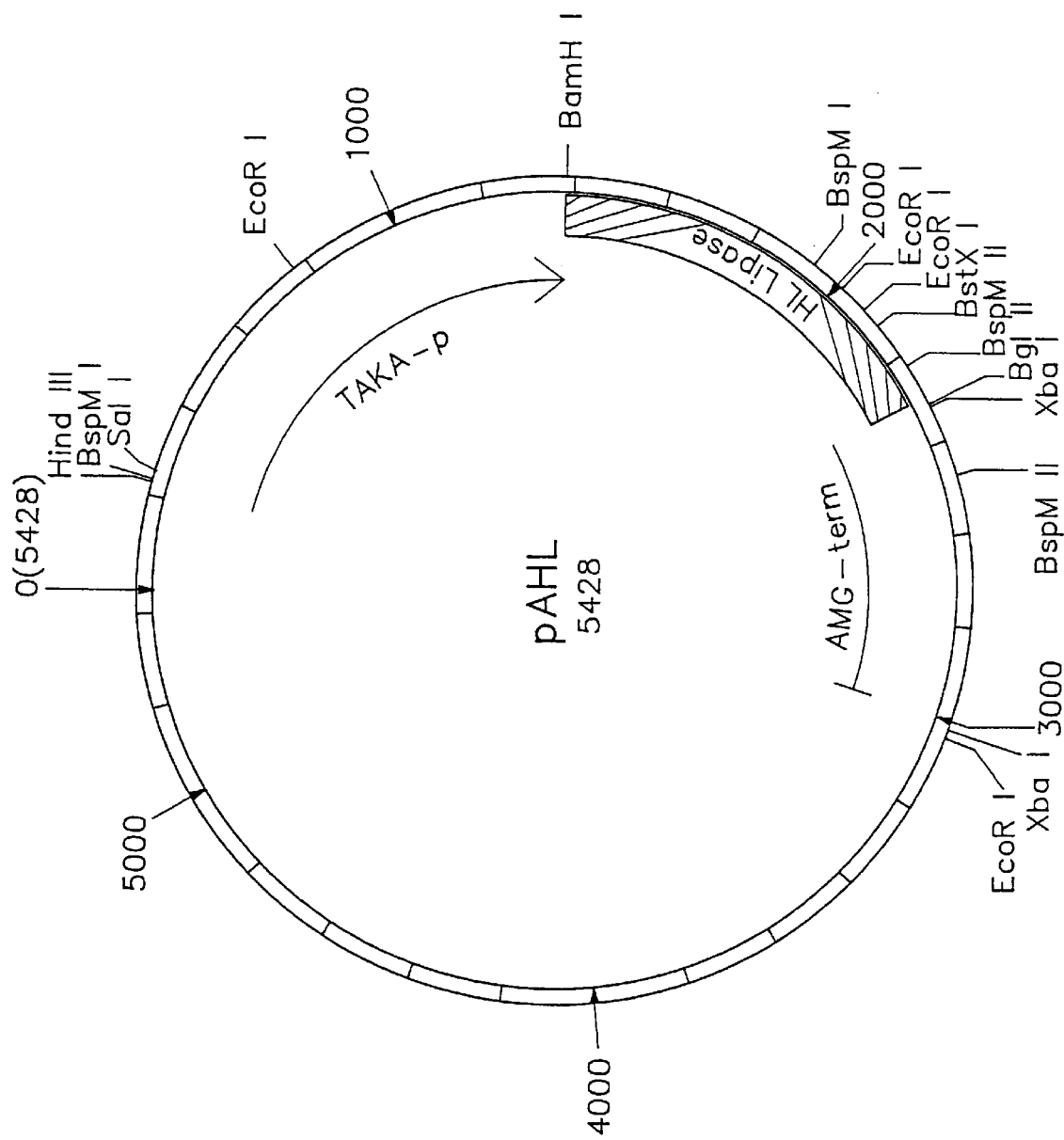

FIG. 1 is a restriction map of pYESHL,

FIG. 2 a restriction map of the plasmid pAO1,

FIG. 3 a restriction map of the plasmid pAHL, and

Figure 4:
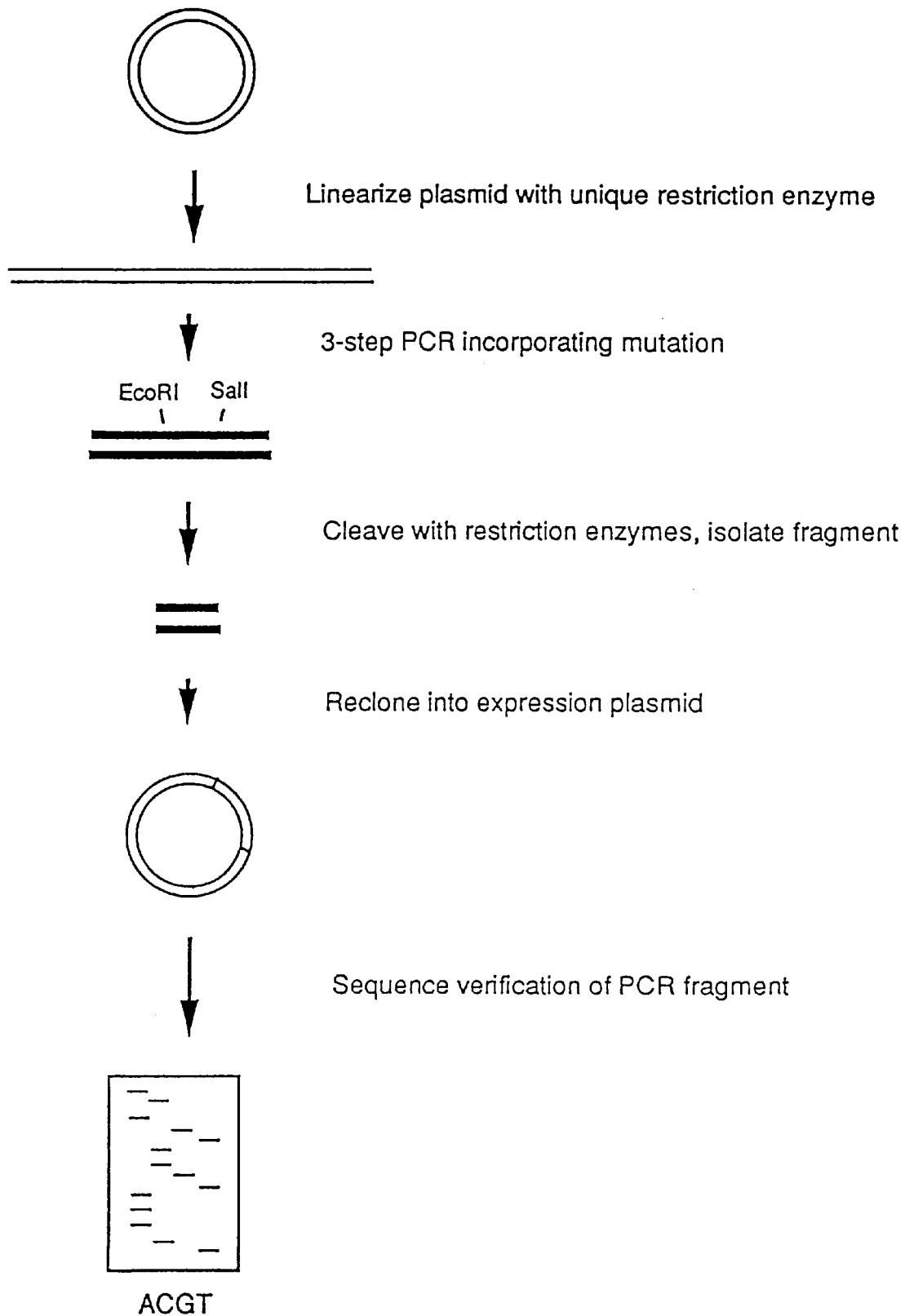
Figure 5:
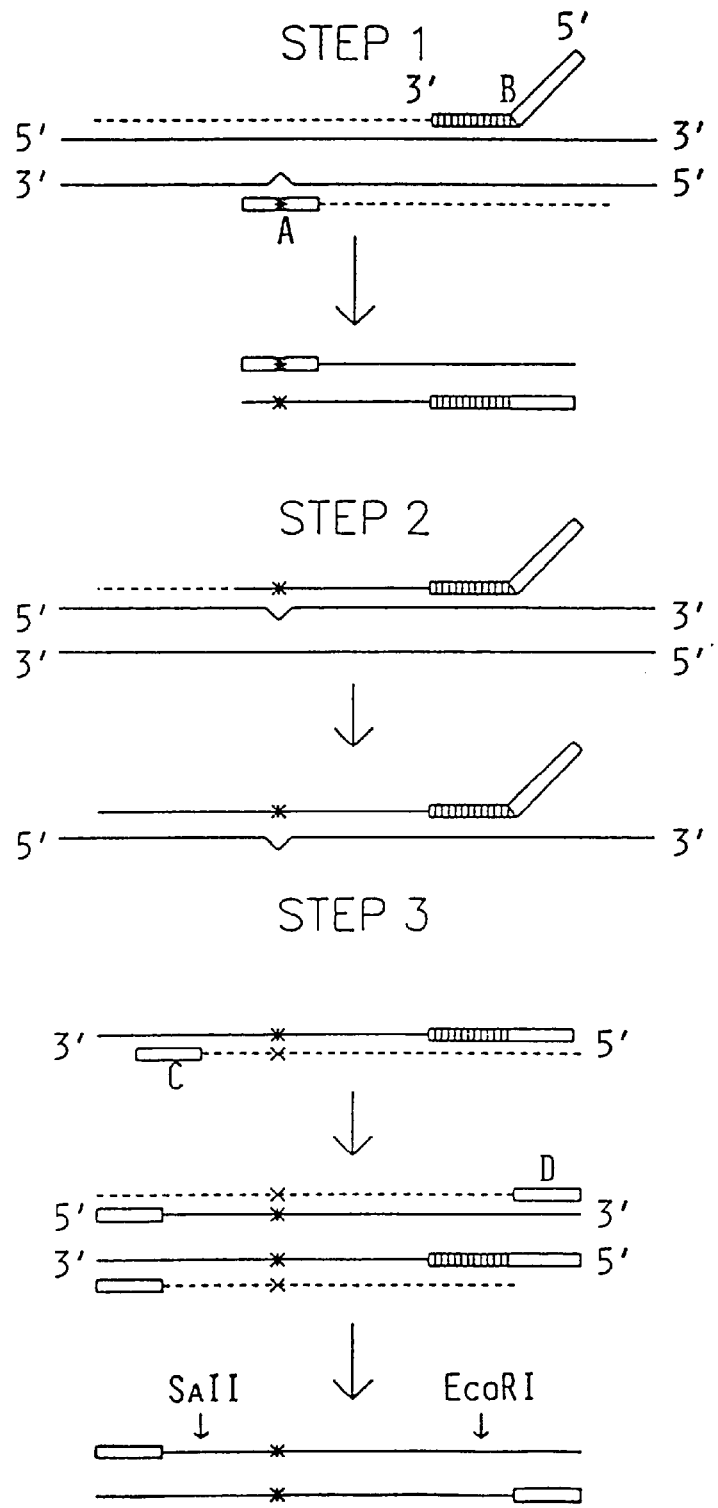

FIGS. 4 and 5 the construction of genes encoding variant of the invention.

The invention is further described in the following examples which are not, in any way, intended to limit the scope of the invention as claimed.

MATERIALS AND METHODS

*Humicola lanuginosa* DSM 4109 available from the Deutsche Sammlung von Mikroorganismen und Zellkulturen GmbH, Mascheroderweg 1b, D-3300 Braunschweig, Federal Republic of Germany.

pYESHL is a yeast/*E. coli* shuttle vector that expresses and secretes a low level of the *H. lanuginosa* lipase in yeast. More specifically pYESHL is a derivative of pYES2 (purchased from Invitrogen Corp., UK) in which the GAL1 promoter was excised and the *Humicola lanuginosa* lipase gene and the TPI (triose phosphate isomerase) promoter from *S. cerevisiae* (Alber, T. and Kawasaki, G., J.Mol.Appl. Genet 1, 419–434 (1982) were cloned between the SphI and XbaI sites. A restriction map of pYESHL is shown in FIG. 1.

Low Calcium Filter Assay

Procedure

1) Provide SC Ura$^-$ replica plates (useful for selecting strains carrying the expression vector) with a first protein binding filter (Nylon membrane) and a second low protein binding filter (Cellulose acetate) on the top.

2) Spread yeast cells containing a parent lipase gene or a mutated lipase gene on the double filter and incubate for 2 or 3 days at 30° C.

3) Keep the colonies on the top filter by transferring the topfilter to a new plate.

4) Remove the protein binding filter to an empty petri dish.

5) Pour an agarose solution comprising an olive oil emulsion (2% P.V.A.:Olive oil=3:1), Brilliant green (indicator, 0.004%), 100 mM tris buffer pH9 and EGTA (final concentration 5 mM) on the bottom filter so as to identify colonies expressing lipase activity in the form of blue-green spots.

6) Identify colonies found in step 5) producing a lipase variant having a reduced dependency for calcium as compared to the parent lipase.

Dobanol™25-7 filter assay:

The screening for an improved tolerance towards a detergent component is performed by use of a filter assay corresponding to that described above except for the fact that the solution defined in 5) further comprises 0.02% Dobanol™25-7.

Construction of Random Mutagenized Libraries a) Using an entire lipase coding gene The plasmid pYESHL is treated with 12 M formic acid for 20 min. at room temperature. The resulting lipase encoding gene is amplified from the formic acid treated plasmid using PCR under mutagenic conditions (0.5 mM $MnCl_2$ and ⅕ the normal amount of ATP, see e.g., Leung et al., 1989.

This treatment is expected to give a broad range of mutations since formic acid gives mainly transversions and PCR generated mutations mainly transitions.

The resulting PCR fragments are cloned either by double recombination (Muhlrad et al., 1992) in vivo into the shuttle vector or digestion and ligation into the shuttle vector and transformation of E. coli.

Eight randomly picked clones have been sequenced and were found to contain 2–3 mutations in average—both transversion and transitions.

By use of this method seven libraries have been made containing from 10,000 to 140,000 clones.

b) Performing localized random mutagenesis

A mutagenic primer (oligonucleotide) is synthesized which corresponds to the part of the DNA sequence to be mutagenized except for the nucleotide(s) corresponding to amino acid codon(s) to be mutagenized.

Subsequently, the resulting mutagenic primer is used in a PCR reaction with a suitable opposite primer. The resulting PCR fragment is purified and digested and cloned into the shuttle vector. Alternatively and if necessary, the resulting PCR fragment is used in a second PCR reaction as a primer with a second suitable opposite primer so as to allow digestion and cloning of the mutagenized region into the shuttle vector. The PCR reactions are performed under normal conditions.

DNA sequencing was performed by using applied Biosystems ABI DNA sequence model 373A according to the protocol in the ABI Dye Terminator Cycle Sequencing kit.

EXAMPLES

Example 1

Construction of Random Lipase Variants

Random mutagenized libraries of the entire H. lanuginosa lipase gene and of amino acids (aa) 91-97 and 206-211 thereof were prepared as described in Materials and Methods above.

The amino acid regions 91-97 and 206-211 were chosen for the first round of localized mutagenesis since these regions have been found to be important for wash performance. Region 91-97 is a part of the lid region of the lipase and region 206-211 constitutes part of the hydrophobic cleft of the lipase.

One oligonucleotide was synthesized for each of these regions comprising 93% of the wild type nucleotides and 2.33% of each of the other three nucleotides at amino acid codons wanted to be mutagenized. Where possible without changing the amino acid, the third nucleotide (the wobble base) in codons were synthesized with 50% G/50% C to give a larger likelyhood for changes to amino acids with one or two codons. The composition of the mutagenic oligonucleotide of region 91-97 is shown in Table 1.

By use of this oligonucleotide a calculated mutation frequency of approximately 65–70% is obtained in the library for one amino acid change having been introduced in the parent lipase. The mutation frequency for two or more amino acid changes having been introduced are less than 35%. This low mutation frequency is chosen to ensure that the observed amino acid changes in positive clones are involved in improving the enzyme and not just "neutral" changes due to a high mutation frequency.

The mutagenic primer were used in a PCR reaction with a suitable opposite primer. The resulting PCR fragment were purified and in the case of region 206-211 digested and cloned into the shuttle vector. In the case of region 91-97 the resulting PCR fragment was used in a second PCR reaction as a primer with a second suitable opposite primer. This step was necessary to be able to digest and clone the mutagenized region into the shuttle vector.

Libraries of region 91-97 and of region 206-211 have been prepared containing from 10,000 to 80.000 clones/library. Most colonies were positive (more than 90%) when checked under conditions where the parent lipase is positive, i.e., exhibits lipase activity. The positive reaction was determined in a filter assay with 2.5 mM Ca (instead of 5 mM EGTA).

450.000 colonies were screened from the different libraries using the Dobanol™25-7 and low calcium assays described in Materials and Methods above. 25 low calcium positives from the aa 91-97 library (lid-region) and twelve Dobanol™25-7 positives from the whole gene libraries were isolated. Fourteen of the low calcium positives from mutagenesis of aa 91-97 were sequenced.

The three other mutations (in codon 83, 103, 145), outside the mutagenized region, can be explained by PCR misincoorperation, allthough the mutation of S83T is a transversion which is quite unusual for PCR misincoorperations.

TABLE 1

Illustration of the construction of oligonucleotides used for localized random mutagensis of amino acids 91–97 of Lipolase ® (SEQ ID NO: 1 and 2). The numbers presented in the sequence refer to the bottles the composition of which is apppearing to the right of the sequence.

Sequence:

| | | | |
|---|---|---|---|
| 5' | 5 | C | G |
| T | 5 | C | 3' |
| T | 7 | A | |
| A | 8 | G | Bottle5: 93% A; 2.33% C; 2.33% G and 2.33% T |
| T | 8 | T | |
| T | A/C | T | |
| T | 5 | C | |
| C | 7 | T | |
| T | 5 | C | Bottle6: 93% C; 2.33% A; 2.33% G and 2.33% T |
| T | 8 | T | |
| T | 8 | A | |
| 6 | C/G | T | |
| 5 | 6 | G | Bottle7: 93% G; 2.33% A; 2.33% C and 2.33% T |
| 5 | 6 | G | |
| 7 | G | A | |
| 8 | A | A | |
| 6 | T | C | Bottle8: 93% T; 2.33% A; 2.33% C and 2.33% G |
| 7 | | | |

TABLE 2

| Strain number | Variant type | | | | |
|---|---|---|---|---|---|
| 59 | I | | G91A | N94K | D96A |
| 60 | II | S83T | | N94K | D96N |

TABLE 2-continued

| Strain number | Variant type | | | | | |
|---|---|---|---|---|---|---|
| 61 | II | S83T | | N94K | | D96N |
| 62 | III | | E87K | | | D96V |
| 63 | IV | | E87K | G91A | | D96V |
| 64 | II | S83T | | | N94K | D96N |
| 65 | III | | E87K | | | D96V |
| 67 | V | | | | N94K F95L | D96H |
| 69 | V | | | | N94K F95L | D96H |
| 71 | III | | E87K | | | D96V |
| 72 | II | S83T | | N94K | | D96N |

Strain number refers to the originally picked clones cloned into Asperfillus expression vector pAHL. Variant type refers to identical clones, which probably have arisen during amplification of the random mutagenized library. Variant types I and II are active in 0.01% Dobanol ™25-7 while the rest are inactive like wild type.

TABLE 3

DNA sequence
(Amino acid number above the sequence)

| Strain number wt | Variant type | 82 GGC | 83 TCT | 84 CGT | 85 TCC | 86 ATA | 87 GAG | 88 AAC | 89 TGG | 90 ATC | 91 GGG | 92 AAT |
|---|---|---|---|---|---|---|---|---|---|---|---|---|
| 59 | I | | | | | | | | | | | c |
| 60 | II | | A | | | | | | | | | c |
| 61 | II | | A | | | | | | | | | c |
| 62 | III | | | | | | A | | | | | c |
| 63 | IV | | | | | | A | | | | c | |
| 64 | II | | A | | | | | | | | | c |
| 65 | III | | | | | | A | | | | | c |
| 67 | V | | | | | | | | | | | c |
| 52/68 | wt | | | | | | | | | | | |
| 53 | wt | | | | | | | | | | | |
| 69 | V | | | | | | | | | | | c |
| 71 | III | | | | | | A | | | | | c |
| 72 | II | | A | | | | | | | | | c |
| 73 | VI | | | | | | | | | | | |

| | | 93 CTT | 94 AAC | 95 TTC | 96 GAC | 97 TTG | 98 AAA | 99 GAA | 100 ATA | -103 -ATT | -145 -CAT |
|---|---|---|---|---|---|---|---|---|---|---|---|
| wt | | | | | | | | | | | |
| 59 | I | G | G | c | | | | | | | |
| 60 | II | G | G | | A | | | | | | |
| 61 | II | G | G | | A | | | | | | |
| 62 | III | | | | T | | | | | | |
| 63 | IV | | | | c | | | | | c | c |
| 64 | II | G | G | | A | | | | | | |
| 65 | III | G | | | T | | | | | | |
| 67 | V | | AC | A | c | | | | | | |
| 52/68 | wt | | | | | | | | | | |
| 53 | wt | | | | | | | | | | |
| 69 | V | | AC | AC | | | | | | | |
| 71 | III | G | | | T | | | | | | |
| 72 | II | G | A | | A | | | | | | |
| 73 | VI | | | | A | ? | | | | | |

Table 3: The wildtype sequence is shown at the topline. Only nucleotides differing from wt are written at the variant sequences. The base of codon 91 and 93 were doped with 1:1 of C/T and T/G, respectively. Otherwise the nucleotides at codon 91–97 were doped using 93% wt and 2.33% of the three other nucleotides.

Example 2

Analogously to the method described in Example 1, the following variants were constructed by random mutagenesis. The actual screening criteria used for selecting some of the variants are also described.

D167G+E210V
5 mM EGTA,0.01% Dobanol™25-7,0.006% LAS
E87K+G91A+L93I+N94K+D96A
5 mM EGTA,0.02% Dobanol™25-7
N73D+S85T+E87K+G91A+N94K+D96A
S83T+E87K+W89G+G91A+N94K+D96V
E87K+G91A+D96R+I100V
S83T+E87K+Q249R
E87K+G91A

Example 3

Expression of *Humicola lanuginosa* Lipase in *Aspergillus oryzae*

Cloning of *Humicola lanuginosa* lipase is described in EP 305 216. It also describes expression and characterization of the lipase in *Aspergillus oryzae*. The expression plasmid used is named p960.

The expression plasmid used in this application is identical to p960, except for minor modifications just 3' to the lipase coding region. The modifications were made the following way: p960 was digested with NruI and BamHI restriction enzymes. Between these two sites the BamHI/NheI fragment from plasmid pBR322, in which the NheI fragment was filled in with Klenow polymerase, was cloned, thereby creating plasmid pAO1 (FIG. 2), which contains unique BamHI and NheI sites. Between these unique sites BamHI/XbaI fragments from p960 was cloned to give pAHL (FIG. 3).

Site-directed in vitro Mutagenesis of Lipase Gene

The approach used for introducing mutations into the lipase gene is described in Nelson & Long, Analytical Biochemistry, 180, 147–151 (1989). It involves the 3-step generation of a PCR (polymerase chain reaction) fragment containing the desired mutation introduced by using a chemically synthesized DNA-strand as one of the primers in the PCR-reactions. From the PCR generated fragment, a DNA fragment carrying the mutation can be isolated by cleavage with restriction enzymes and re-inserted into the expression plasmid. This method is thoroughly described in Example 5. In FIGS. 4 and 5 the method is further outlined.

Construction of a Plasmid Expressing the N94K/D96A Analogue of *Humicola lanuginosa* Lipase Linearization of Plasmid pAHL The circular plasmid pAHL is linearized with the restriction enzyme SphI in the following 50 µl reaction mixture: 50 mM NaCl, 10 mM Tris-HCl, pH 7.9, 10 mM $MgCl_2$, 1 mM dithiothreitol, 1 µg plasmid and 2 units of SphI. The digestion is carried out for 2 hours at 37° C. The reaction mixture is extracted with phenol (equilibrated with Tris-HCl, pH 7.5) and precipitated by adding 2 volumes of ice-cold 96% ethanol. After centrifugation and drying of the pellet, the linearized DNA was dissolved in 50 µl $H_2O$ and the concentration estimated on an agarose gel.

3-step PCR Mutagenesis

As shown in FIG. 5, 3-step mutagenisation involves the use of four primers:

Mutagenisation primer (=A): 5'-TATTTCTTTCAAAGCGAACTTAAGATTCCCGAT-3' (SEQ ID NO:3)

PCR Helper 1 (=B): 5'-GGTCATCCAGTCACTGAGACCCTCTACCTATTAAATCGGC-3' (SEQ ID NO:4)

PCR Helper 2 (=C): 5'-CCATGGCTTTCACGGTGTCT-3' (SEQ ID NO:5)

PCR Handle (=D): 5'-GGTCATCCAGTCACTGAGAC-3' SEQ ID NO:6)

Helper 1 and helper 2 are complementary to sequences outside the coding region, and can thus be used in combination with any mutagenisation primer in the construction of a variant sequence.

All 3 steps are carried out in the following buffer containing: 10 mM Tris-HCl, pH 8.3, 50 mM KCl, 1.5 mM MgCl$_2$, 0.001% gelatin, 0.2 mM dATP, 0.2 mM dCTP, 0.2 mM dGTP, 0.2 mM TTP, 2.5 units Taq polymerase.

In step 1, 100 pmol primer A, 100 pmol primer B and 1 fmol linearized plasmid is added to a total of 100 μl reaction mixture and 15 cycles consisting of 2 minutes at 95° C., 2 minutes at 37° C. and 3 minutes at 72° C. are carried out.

The concentration of the PCR product is estimated on an agarose gel. Then, step 2 is carried out. 0.6 pmol step 1 product and 1 fmol linearized plasmid is contained in a total of 100 μl of the previously mentioned buffer and 1 cycle consisting of 5 minutes at 95° C., 2 minutes at 37° C. and 10 minutes at 72° C. is carried out.

To the step 2 reaction mixture, 100 pmol primer C and 100 pmol primer D is added (1 μl of each) and 20 cycles consisting of 2 minutes at 95° C., 2 minutes at 37° C. and 3 minutes at 72° C. are carried out. This manipulation comprised step 3 in the mutagenisation procedure.

Isolation of Mutated Restriction Fragment

The product from step 3 is isolated from an agarose gel and re-dissolved in 20 μl H$_2$O. Then, it is digested with the restriction enzymes BamHI and BstXI in a total volume of 50 μl with the following composition: 100 mM NaCl, 50 mM Tris-HCl, pH 7.9, 10 mM MgCl$_2$, 1 mM DTT, 10 units of BamHI and 10 units of BstXI. Incubation is at 37° C. for 2 hours. The 733 bp BamHI/BstXI fragment is isolated from an agarose gel.

Ligation to Expression Vector pAHL

The expression plasmid pAHL is cleaved with BamHI and BstXI under conditions indicated above and the large fragment is isolated from an agarose gel. To this vector, the mutated fragment isolated above is ligated and the ligation mix is used to transform *E. coli*. The presence and orientation of the fragment is verified by cleavage of a plasmid preparation from a transformant with restriction enzymes. Sequence analysis is carried out on the double-stranded plasmid using the DyeDeoxy™ Terminater Cycle Sequencing Kit (Applied Biosystems) on an ABI DNA sequencer, model 373A. The plasmid is named pAHLG91A/N94K/D96A and is identical to pAHL, except for the substituted codons.

Example 4

Construction of Plasmids Expressing Other Variants of *Humicola lipase*

The following variant is constructed using the same method as described in example 3. Plasmid name and primer used for the modification is listed below.

| Plasmid name | Primer A sequence | |
|---|---|---|
| pAHLS83T/N94K/D96A | 5'-ATTTCTTTCAAAGCGAACTTAAGATTCCCGATCCAGTTCTCTATG GAACGAGTGCCACGGAAAGA-3' | (SEQ ID NO:7) |
| pAHLE87K/D96V | 5-TATTTCTTTCAAAACGAAGTTAAGATTCCCGATCCAGTTCTTTAT GGAACGAGA-3' | (SEQ ID NO:8) |
| pAHLE87K/G91A/D96A | 5'-TATTTCTTTCAAAGCGAAGTTAAGATTAGCGATCCAGTTCTTTAT GGAACGAGA-3 | (SEQ ID NO:9) |
| pAHLN94K/F95L/D96H | 5'-TATTTCTTTCAAGTGCAACTTAAGATTCCCGAT-3' | (SEQ ID NO:10) |
| pAHLF95C/D96N | 5'-TATTTCTTTCAAGTTACAGTTAAGATTCCC-3' | (SEQ ID NO:11) |
| pAHLG91S/L93V/F95C | 5'-TATTTCTTTCAAGTCACAGTTAACATTAGAGATCCAGTTCTC-3' | (SEQ ID NO:12) |
| pAHLE87K/G91A/L93I/N94K/D96A | 5'-TATTTCTTTCAAAGCGAACTTAATATTAGCGATCCAGTTCTTTAT GGAACGAGA-3' | (SEQ ID NO:13) |
| pAHLD167G | 5'-ATATGAAAACACACCGATATCATACCC-3' | (SEQ ID NO:14) |
| pAHLA121V | 5'-CCTTAACGTATCAACTACAGACCTCCA-3' | (SEQ ID NO:15) |
| pAHLR205K/E210Q | 5'-GCTGTAACCGAATTGGCGCGGCGGGAGCTTAGGGACAATATC-3' | (SEQ ID NO:16) |
| pAHLN73D/S85T/E87K/G91A/N94K/D96A | 5'-TATTTCTTTCAAAGCGAACTTAAGATTAGCGATCCAGTTCTTTAT AGTACGAGAGCCACGGAAAGAGAGGACGATCAATTTGTCCGTGTTG TCGAG-3' | (SEQ ID NO:17) |
| pAHLS83T/E87K/W89G/G91A/N94K/D96V | 5'-TATTTCTTTCAAAACGAACTTAAGATTAGCGATACCGTTCTTTAT GGAACGAGTGCCACGGAAAGA-3' | (SEQ ID NO:18) |
| pAHLE87K/G91A/D96R/I100V | 5'-GCAAATGTCATTAACTTCTTTCAATCTGAAGTTAAGATTAGCGAT CCAGTTCTTTATGGAACGAGA-3' | (SEQ ID NO:19) |
| pAHLS83T/E87K | 5'-CCCGATCCAGTTCTTTATGGAACGAGTGCCACGGAAAGA-3' | (SEQ ID NO:20) |
| pAHLE87K/G91A | 5'-GAAGTTAAGATTAGCGATCCAGTTCTTTATGGAACGAGA-3' | (SEQ ID NO:21) |
| pAHLS83T/E87K | 5'-CCCGATCCAGTTCTTTATGGAACGAGTGCCACGGAAAGA-3' | (SEQ ID NO:22) |
| pAHLQ249R | 5'-CGGAATGTTAGGTCTGTTATTGCCGCC-3' | (SEQ ID NO:23) |

Example 5

Construction of Plasmids Expressing Combination Analogues of *Humicola lipase*

The plasmids pAHLD167G/E210V, pAHLA121V/R205K/E210Q and pAHLS83T/E87K/Q249R are constructed by performing two successive mutagenisation steps using the appropriate primers.

Example 6

Expression of Lipase Analogues in Aspergillus

Transformation of *Aspergillus oryzae* (general procedure)

100 ml of YPD (Sherman et al., Methods in Yeast Genetics, Cold Spring Harbor Laboratory, 1981) is inoculated with spores of *A. oryzae* and incubated with shaking for about 24 hours. The mycelium is harvested by filtration through miracloth and washed with 200 ml of 0.6 M $MgSO_4$. The mycelium is suspended in 15 ml of 1.2 M $MgSO_4$, 10 mM $NaH_2PO_4$, pH=5.8. The suspension is cooled on ice and 1 ml of buffer containing 120 mg of Novozym® 234, batch 1687 is added. After 5 min., 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayed with 5 ml of 0.6 M sorbitol, 100 mM Tris-HCl, pH=7.0. Centrifugation is performed for 15 min. at 1000 g and the protoplasts are collected from the top of the $MgSO_4$ cushion. 2 volumes of STC (1.2 M sorbitol, 10 mM Tris-HCl, pH=7.5, 10 mM $CaCl_2$) are added to the protoplast suspension and the mixture is centrifugated for 5 min. at 1000 g. The protoplast pellet is resuspended in 3 ml of STC and repelleted. This is repeated. Finally, the protoplasts are resuspended in 0.2–1 ml of STC.

100 μl of protoplast suspension is mixed with 5–25 μg of p3SR2 (an *A. nidulans* amdS gene carrying plasmid described in Hynes et al., Mol. and Cel. Biol., Vol. 3, No. 8, pp. 1430–39, August 1983) in 10 μl of STC. The mixture is left at room temperature for 25 min. 0.2 ml of 60% PEG 4000 (BDH 29576), 10 mM $CaCl_2$ and 10 mM Tris-HCl, pH=7.5 is added and carefully mixed (twice) and finally 0.85 ml of the same solution is added and carefully mixed. The mixture is left at room temperature for 25 min., spun at 2.500 g for 15 min. and the pellet is resuspended in 2 ml of 1.2 M sorbitol. After one more sedimentation the protoplasts are spread on minimal plates (Cove, Biochem. Biophys. Acta 113 pp. 51–56 (1966)) containing 1.0 M sucrose, pH=7.0, 10 mM acetamide as nitrogen source and 20 mM CsCl to inhibit background growth. After incubation for 4–7 days at 37° C. spores are picked, suspended in sterile water and spread for single colonies. This procedure is repeated and spores of a single colony after the second reisolation are stored as a defined transformant.

Expression of Lipase Analogues in *A. oryzae*

The plasmids described above are transformed into *A. oryzae* IFO 4177 by cotransformation with p3SR2 containing the amdS gene from *A. nidulans* as described in the above example. Protoplasts prepared as described are incubated with a mixture of equal amounts of expression plasmid and p3SR2, approximately 5 μg of each are used. Transformants which could use acetamide as sole nitrogen source are reisolated twice. After growth on YPD for three days, culture supernatants are analyzed using an assay for lipase activity. The best transformant is selected for further studies and grown in a 1 l shake-flask on 200 ml FG4 medium (3% soy meal, 3% maltodextrin, 1% peptone, pH adjusted to 7.0 with 4 M NaOH) for 4 days at 30° C.

Example 7

Purification of Lipase Variants of the Invention

Assay for lipase activity:

A substrate for lipase was prepared by emulsifying glycerine tributyrat (MERCK) using gum-arabic as emulsifier.

Lipase activity was assayed at pH 7 using pH stat method. One unit of lipase activity (LU/mg) was defined as the amount needed to liberate one micromole fatty acid per minute.

Step 1: Centrifuge the fermentation supernatant, discard the precipitate. Adjust the pH of the supernatant to 7 and add gradually an equal volume of cold 96% ethanol. Allow the mixture to stand for 30 minutes in an ice bath. Centrifuge and discard the precipitate.

Step 2: Ion exchange chromatography. Filter the supernatant and apply on DEAE-fast flow (Pharmacia TM) column equilibrated with 50 mM tris-acetate buffer pH 7. Wash the column with the same buffer till absorption at 280 nm is lower than 0.05 OD. Elute the bound enzymatic activity with linear salt gradient in the same buffer (0 to 0.5 M NaCl) using five column volumes.

Pool the fractions containing enzymatic activity.

Step 3: Hydrophobic chromatography. Adjust the molarity of the pool containing enzymatic activity to 0.8 M by adding solid Ammonium acetate. Apply the enzyme on TSK gel Butyl-Toyopearl 650 C column (available from Tosoh Corporation Japan) which was pre-equilibrated with 0.8 M ammonium acetate. Wash the unbound material with 0.8 M ammonium acetate and elute the bound material with distilled water.

Step 4: Pool containing lipase activity is diluted with water to adjust conductance to 2 mS and pH to 7. Apply the pool on High performance Q Sepharose (Pharmacia) column pre-equilibrated with 50 mM tris-acetate buffer pH 7. Elute the bound enzyme with linear salt gradient.

Example 8

The washing Performance of Lipase Variants of the Invention

The washing performance of *Humicola lanuginosa* lipase variants of the invention was evaluated on the basis of the enzyme dosage in mg of protein per liter according to $OD_{280}$ compared to the wild-type *H. lanuginosa* lipase.

Wash trials were carried out in 150 ml beakers placed in a thermostated water bath. The beakers were stirred with triangular magnetic rods.

The experimental conditions were as follows:

Method: 3 cycles with overnight drying between each cycle

Wash liquor: 100 ml per beaker

Swatches: 6 swatches (3.5×3.5 cm) per beaker

Fabric: 100% cotton, Test Fabrics style #400

Stain: Lard coloured with Sudan red (0.75 mg dye/g of lard). 6 μl of lard heated to 70° C. was applied to the centre of each swatch. After application of the stain, the swatches were heated in an oven at 75° C. for 30 minutes. The swatches were then stored overnight at room temperature prior to the first wash.

Detergent: LAS (Nansa 1169/P, 30% a.m.) 1.17 g/l

AEO (Dobanol™25-7) 0.15 g/l

Sodium triphosphate 1.25 g/l

Sodium sulphate 1.00 g/l

Sodium carbonate 0.45 g/l

Sodium silicate 0.15 g/l pH: 10.2
Lipase conc.: 0.075, 0.188, 0.375, 0.75 and 2.5 mg of lipase protein per liter
Time: 20 minutes
Temperature: 30° C.
Rinse: 15 minutes in running tap water
Drying: overnight at room temperature (~20° C., 30–50% RH)
Evaluation: after the 3rd wash, the reflectance at 460 nm was measured.

Results

Dose-response curves were compared for the lipase variants and the native H. lanuginosa lipase. The dose-response curves were calculated by fitting the measured data to the following equation:

$$\Delta R = \Delta R_{max} \frac{C^{0.5}}{K + C^{0.5}} \qquad (I)$$

where ΔR is the effect expressed in reflectance units

C is the enzyme concentration (mg/l)

$\Delta R_{max}$ is a constant expressing the maximum effect

K is a constant; $K^2$ expresses the enzyme concentration at which half of the maximum effect is obtained.

Based on the characteristic constants $\Delta R_{max}$ and K found for each lipase variant as well as the wild-type lipase, improvement factors were calculated. The improvement factor, defined as $$f_{improve} = C_{WT}/C \qquad (II)$$

expresses the amount of lipase variant protein needed to obtain the same effect as that obtained with 0.25 mg/l of the reference wild-type protein ($C_{WT}$).

Thus, the procedure for calculating the improvement factor was as follows:

1) The effect of the wild-type protein at 0.25 mg/l ($\Delta R_{wild-type}$) was calculated by means of equation (I);
2) the concentration of lipase variant resulting in the same effect as the wild-type at 0.25 mg/l was calculated by means of the following equation:

$$C = \left( K_{(analogue)} \frac{\Delta R_{(wild-type)}}{\Delta R_{max(analogue)} - \Delta R_{(wild-type)}} \right)^2 \qquad (III)$$

3) the improvement factor was calculated by means of equation (II).

The results are shown in Table IV below.

TABLE IV

| Variant | Improvement factor |
| --- | --- |
| E87K + D96V | 1.2 |
| S83T + N94K + D96N | 2.3 |
| N94K + D96A | 2.7 |
| E87K + G91A + D96A | 2.6 |
| N94K + F95L + D96H | 3.3 |
| D167G + E210V | 5.0 |
| E87K + G91A + L93I + N94K + D96A | 1.3 |
| E87K + G91A + D96R + I100V | 5.2 |
| E87K + G91A | 5.0 |
| N73D + E87K + G91A + N94I + D96G | 1.3 |
| S83T + E87K + G91A + N92H + N94K + D96M | 3.8 |
| K46R + E56R + G61S | 1.9 |

TABLE IV-continued

| Variant | Improvement factor |
| --- | --- |
| D102K | 0.2 |
| D167G | 1 |
| N73D + E87K + G91A + N94I + D96G | 1.3 |
| E210R | 2.7 |
| E210K | 5.5 |
| E210W | 1 |
| N251W + D254W + T267W | 0.8 |
| S83T + E87K + G91A + N92H + N94K + D96M | 3.8 |
| E56R + I90F + D96L + E99K | 4.8 |
| D57G + N94K + D96L + L97M | 1.9 |

REFERENCES CITED IN THE SPECIFICATION

Muhlrad et al., 1992, Yeast, Vol. 8, 79–82

Shimada, Y. et al. (1989). cDNA Molecular Cloning of Geotrichum candidum Lipase. J. Biochem., 106, 383–388.

Yamaguchi, S. et al. (1991). Cloning and structure of the mono- and diglycerol lipase-encoding gene from Penicillium camembertii U-150. Gene 103, 61–67.

Hass, M. J. et al. (1991). Cloning, expression and characterization of a cDNA encoding a lipase from Rhizopus delemar. Gene 109, 107–113.

Kugimiya, W. et al. (1992). Cloning and Sequences Analysis of DNA encoding Rhizopus niveus Lipase. Biosci. Biotech. Biochem. 56, 716–719.

Dartois, V. et al. (1993). Cloning, nucleotide sequence and expression in Escherichia coli of a lipase gene from Bacillus subtilis 168. Biochemica et Biophysica acta 1131, 253–260.

Sambrook et al. Molecular Cloning: A Laboratory Manual, 2nd Ed., Cold Spring Harbor, 1989.

R. K. Saiki et al., Science 239, pp. 487–491, 1988.

Beaucage and Caruthers, Tetrahedron Letters 22, pp. 1859–1869, 1981.

Matthes et al., The EMBO J. 3, pp. 801–805, 1984.

J. O. Deshler, (1992) A simple method for randomly mutating cloned DNA fragments by using chemical mutagens and the polymerase chain reaction. GATA 9(4): 103–106.

Leung et al., Technique, Vol. 1, No. 1, pp. 11–15, 1989.

Fowler et al., Molec. gen. Genet., 133, pp. 179–191, 1974.

Brady et al., "A Serine Protease Triad Forms the Catalytic Centre of a Triacylglycerol Lipase", Nature 343, 1990, pp. 767–770, 1990.

Tilbeyrgh, H. van, Egloff, M.-P., Martinez, C., Rugani, N., Verger, R. and Cambillau (1993) Nature 362, p. 814–820. Interfacial activation of the lipase-prolipase complex by mixed micelles revealed by X-ray crystallography.

Hudson et al., Practical Immunology, Third edition, Blackwell Scientific Publications, 1989.

Alber, T. and Kawasaki, G., J.Mol.Appl. Genet 1, 419–434 (1982).

We claim:

1. A method of preparing a variant of a final lipolytic enzyme, which comprises
   (a) subjecting a DNA sequence encoding the fungal lipolytic enzyme to random mutagenesis,
   (b) expressing the mutated DNA sequence obtained in step (a) in a host cell, and
   (c) screening for host cells expressing a mutated lipolytic enzyme which requires lower amounts of calcium for exhibiting the same degree of activity.

2. The method according to claim 1, in which the random mutagenesis is performed by use of a physical or a chemical mutagenizing agent, by use of an oligonucleotide or by use of PCR generated mutagenesis.

3. The method according to claim 1, in which the mutagenizing agent is selected from formic acid, UV irradiation, hydroxylamine, N-methyl-N'-nitro-N-nitrosoguanidine (MNNG), O-methyl hydroxylamine, nitrous acid, ethyl methane sulphonate (EMS), sodium bisulphite, and nucleotide analogues.

4. The method according to claim 1, in which the mutated DNA sequence is expressed by transforming a suitable host cell with the mutated DNA sequence and culturing the host cell obtained in step (b) under suitable conditions for expressing the mutated DNA sequence.

5. The method according to claim 1, in which the host cell is a microbial cell.

6. The method according to claim 5, in which the host cell is a fungal or bacterial cell.

7. The method according to claim 6, in which the host cell is an Aspergillus cell.

8. The method according to claim 6, in which the host cell is a Bacillus cell.

9. The method according to claim 1, in which the variant has an improved tolerance towards a non-ionic, anionic, cationic, zwitterionic or amphoteric surfactant.

10. The method according to claim 9, in which the non-ionic surfactant is an alcohol ethoxylate and the anionic surfactant is a linear alkylbenzenesulfonate or an alkyl sulphate.

11. The method according to claim 1, wherein host cells screened in step (c) are subjected to a second mutagenesis treatment, to rescreening, to reisolation and to recloning.

12. The method according to claim 1, in which the random mutagenesis is localized to a part of the DNA sequence encoding the fungal lipolytic enzyme.

13. The method according to claim 1, in which the fungal lipolytic enzyme is a lipase, esterase, cutinase or phospholipase.

14. The method according to claim 13, in which the parent lipolytic enzyme is a lipase and the localized random mutagenesis is performed on a part of the DNA sequence encoding a lipid contact zone of the lipase or a part thereof.

15. The method according to claim 13, in which the localized random mutagenesis is performed on a part of the DNA sequence encoding a lid region and a hydrophobic cleft of the lipase or a part thereof.

16. The method according to claim 1, wherein the parent lipolytic enzyme is a Humicola sp., Rhizomucor sp., Rhizopus sp., Candida sp. lipolytic enzyme.

17. The method according to claim 16, wherein the parent lipolytic enzyme is a H. lanuginosa, Rh. mucor, or C. antarctica lipase.

18. The method according to claim 17, in which the lipase is obtained from DSM 4109 and the DNA sequence is mutated in at least one of the regions defined by the amino acid residues 21–27, 56–64, 81–99, 108–116, 145–147, 174, 202–213, 226–227, 246–259 or 263–269.

19. The method according to claim 18, in which the localized random mutagenesis is performed in at least two of the regions.

20. In a method of subjecting a DNA sequence encoding a fungal lipolytic enzyme to random mutagenesis and expressing the mutated DNA sequence in a host cell, the improvement comprising screening for host cells expressing a mutated lipolytic enzyme which requires lower amounts of calcium for exhibiting the same degree of activity than the parent lipolytic enzyme.

21. The method of claim 1, futher comprising screening for host cells expressing a mutated lipolytic enzyme which has an improved tolerance towards a detergent or a detergent component as compared to the parent lipolytic enzyme.

* * * * *